US012653884B2

(12) United States Patent
Rothstein et al.

(10) Patent No.: US 12,653,884 B2
(45) Date of Patent: Jun. 16, 2026

(54) ANTI-CD154 ANTIBODY HAVING IMPROVED BINDING, FUNCTIONAL AND SAFETY CHARACTERISTICS AND USE IN HUMAN IMMUNOTHERAPY

(71) Applicant: IMMUNEXT, INC., Lebanon, NH (US)

(72) Inventors: Jay Rothstein, Norwich, VT (US); Robert George Edward Holgate, Royston (GB); Arron Hearn, Ely (GB)

(73) Assignee: IMMUNEXT, INC., Lebanon, NH (US)

( * ) Notice: Subject to any disclaimer, the term of this patent is extended or adjusted under 35 U.S.C. 154(b) by 690 days.

(21) Appl. No.: 18/162,769

(22) Filed: Feb. 1, 2023

(65) Prior Publication Data

US 2024/0000929 A1 Jan. 4, 2024

Related U.S. Application Data

(62) Division of application No. 17/101,139, filed on Nov. 23, 2020, now Pat. No. 11,596,689, which is a division of application No. 15/744,379, filed as application No. PCT/US2016/042074 on Jul. 13, 2016, now Pat. No. 10,874,738.

(60) Provisional application No. 62/277,201, filed on Jan. 11, 2016, provisional application No. 62/197,966, filed on Jul. 28, 2015, provisional application No. 62/192,269, filed on Jul. 14, 2015.

(51) Int. Cl.
| | |
|---|---|
| *A61K 39/395* | (2006.01) |
| *C07K 16/28* | (2006.01) |
| *A61K 38/00* | (2006.01) |
| *A61K 39/00* | (2006.01) |

(52) U.S. Cl.
CPC ........ *A61K 39/3955* (2013.01); *A61K 39/395* (2013.01); *C07K 16/2875* (2013.01); *A61K 38/00* (2013.01); *A61K 2039/505* (2013.01); *C07K 2317/24* (2013.01); *C07K 2317/565* (2013.01); *C07K 2317/71* (2013.01); *C07K 2317/92* (2013.01); *G01N 2800/52* (2013.01)

(58) Field of Classification Search
CPC ...................... A61K 39/3955; C07K 16/2875
See application file for complete search history.

(56) References Cited

U.S. PATENT DOCUMENTS

| | | | |
|---|---|---|---|
| 7,169,389 B2 | 1/2007 | Di Padova et al. | |
| 7,429,644 B2 | 9/2008 | Garber et al. | |
| 9,321,833 B2 | 4/2016 | Noelle et al. | |
| 10,874,738 B2 | 12/2020 | Rothstein et al. | |
| 2004/0038293 A1 | 2/2004 | Di Padova et al. | |
| 2004/0058394 A1 | 3/2004 | Garber et al. | |
| 2006/0147446 A1 | 7/2006 | Black et al. | |
| 2008/0124278 A1 | 5/2008 | Taylor et al. | |
| 2013/0108621 A1* | 5/2013 | Noelle .................. | A61K 39/00 |
| | | | 530/387.3 |
| 2013/0136734 A1 | 5/2013 | Noelle et al. | |

FOREIGN PATENT DOCUMENTS

| | | |
|---|---|---|
| WO | 99/12566 A1 | 3/1999 |
| WO | 2008118356 A2 | 10/2008 |

OTHER PUBLICATIONS

Jefferis R. Glycosylation as a strategy to improve antibody-based therapeutics. Nature reviews Drug discovery. Mar. 2009;8(3):226-34.
Kiyoshi M, Caaveiro JM, Tada M, Tamura H, Tanaka T, Terao Y, Morante K, Harazono A, Hashii N, Shibata H, Kuroda D. Assessing the heterogeneity of the Fc-glycan of a therapeutic antibody using an engineered FcγReceptor IIIa-immobilized column. Scientific reports. Mar. 2, 2018;8(1):1-1.
Wang X, Mathieu M, Brezski RJ. IgG Fc engineering to modulate antibody effector functions. Protein & cell. Jan. 2018;9(1):63-73.
Saunders KO. Conceptual approaches to modulating antibody effector functions and circulation half-life. Frontiers in immunology. Jun. 7, 2019;10:1296.
Kirk AD, et al., "Treatment with humanized monoclonal antibody against CD154 prevents acute renal allograft rejection in nonhuman primates", Nature Med. Jun. 1999;5(6):686-93.
Burkly LC. "CD40 pathway blockade as an approach to immunotherapy", Adv Exp Med Biol. 2001;489:135-52.
Kuwana M, et al. "Effect of a single injection of humanized anti-CD154 monoclonal antibody on the platelet-specific autoimmune response in patients with immune thrombocytopenia purpura," Blood. Feb. 15, 2004;103(4):1229-36.

* cited by examiner

*Primary Examiner* — Xiaozhen Xie

(74) *Attorney, Agent, or Firm* — Robin L. Teskin; Baker, Donelson, Bearman, Caldwell & Berkowitz PC

(57) ABSTRACT

Improved anti-CD 154 antibodies are provided herein which have improved therapeutic potency, in vivo half-life and ablated FcR binding and/or complement binding/activation. The use of these antibodies for inducing tolerance and treating immune diseases including autoimmunity, inflammation, transplant recipients, fibrosis and allergic disorders is disclosed herein.

Figure 2B:
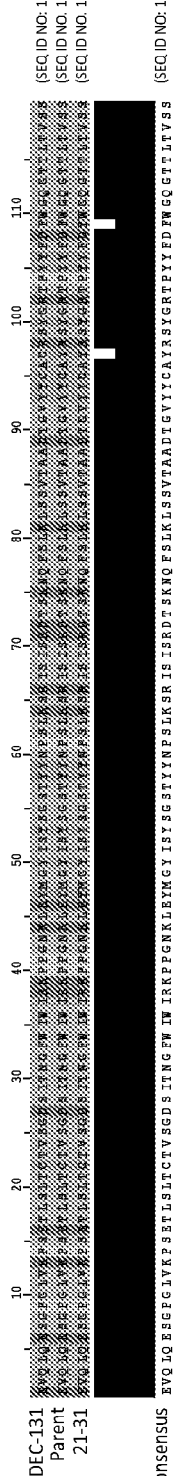

9 Claims, 15 Drawing Sheets
Specification includes a Sequence Listing.

FIGURE 1A

Heavy Chain

Variable region shown in bold
CDRs highlighted in yellow
Affinity maturation mutated residues <u>underlined</u>
Fc mutations (E→R and K→A) shown in red

```
        10          20          30          40          50          60
EVQLQESGPG  LVKPSETLSL  TCTVSGDSIT  NGFWIWIRKP  PGNKLEYMGY  ISYSGSTYYN 70          80          90         100         110         120
PSLKSRISIS  RDTSKNQFSL  KLSSVTAADT  GVYYCAYRSY  GRTPYYFDYW  GQGTTLTVSS 130         140         150         160         170         180
ASTKGPSVFP  LAPSSKSTSG  GTAALGCLVK  DYFPEPVTVS  WNSGALTSGV  HTFPAVLQSS 190         200         210         220         230         240
GLYSLSSVVT  VPSSSLGTQT  YICNVNHKPS  NTKVDKKAEP  KSCDKTHTCP  PCPAPELLGG 250         260         270         280         290         300
PSVFLFPPKP  KDTLMISRTP  EVTCVVVDVS  HRDPEVKFNW  YVDGVEVHNA  KTKPREEQYN 310         320         330         340         350         360
STYRVVSVLT  VLHQDWLNGK  EYKCAVSNKA  LPAPIEKTIS  KAKGQPREPQ  VYTLPPSRDE 370         380         390         400         410         420
LTKNQVSLTC  LVKGFYPSDI  AVEWESNGQP  ENNYKTTPPV  LDSDGSFFLY  SKLTVDKSRW 430         440         450
QQGNVFSCSV  MHEALHNHYT  QKSLSLSPGK
```

FIGURE 1B

<u>Light Chain</u>

Variable region shown in bold
CDRs highlighted in yellow
Affinity maturation mutated residues <u>underlined</u>

```
        10          20          30          40          50          60
DIVMTQSPSF  LSASVGDRVT  ITCKASSNLG  HAVAWYQQKP  GKSPKLLIYS  ASNRYTGVPD 70          80          90         100         110         120
RFSGSGSGTD  FTLTISSLQP  EDFADYFCQQ  YDDYPYTFGG  GTKLEIKRTV  AAPSVFIFPP 130         140         150         160         170         180
SDEQLKSGTA  SVVCLLNNFY  PREAKVQWKV  DNALQSGNSQ  ESVTEQDSKD  STYSLSSTLT 190         200         210
LSKADYEKHK  VYACEVTHQG  LSSPVTKSFN  RGEC
```

FIGURE 1C

<u>INX021 Sequences</u>

Variable Heavy (SEQ ID NO. 1)
EVQLQESGPGLVKPSETLSLTCTVSGDSITNGFWIWIRKPPGNKLEYMGYISYSGSTYYNPSLKSRISISR
DTSKNQFSLKLSSVTAADTGVYYCAYRSYGRTPYYFDYWGQGTTLTVSS

Variable Light (SEQ ID NO. 2)
DIVMTQSPSFLSASVGDRVTITCKASSNLGHAVAWYQQKPGKSPKLLIYSASNRYTGVPDRFSGSGSGTDF
TLTISSLQPEDFADYFCQQYDDYPYTFGGGTKLEIK

Constant Heavy (SEQ ID NO. 3)
ASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKAEPKSCDKTHTCPPCPAPELLGGPSVFLFPPKPKDTLMISRTPEV
TCVVVDVSHRDPEVKFNWYVDGVEVHNAKTKPREEQYNSTYRVVSVLTVLHQDWLNGKEYKCAVSNKALPA
PIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK

Constant Light (SEQ ID NO. 4)
RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC

INX021 Variable Heavy CDR1 (SEQ ID NO: 5)
GDSITNGFWI

INX021 Variable Heavy CDR2 (SEQ ID NO: 6)
YISYSGSTY

INX021 Variable Heavy CDR3 (SEQ ID NO: 7)
YRSYGRTPYYFDY

INX021 Variable Light CDR1 (SEQ ID NO: 8)
KASSNLGHAVA

INX021 Variable Light CDR2 (SEQ ID NO: 9)
SASNRYT

INX021 Variable Light CDR3 (SEQ ID NO: 10)
QQYDDYPYT

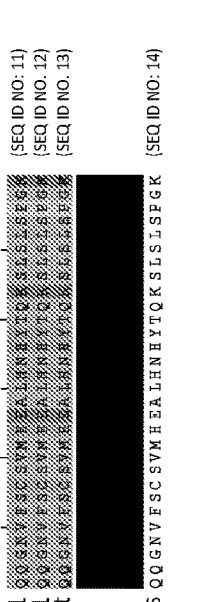

Constant heavy-chain sequences

Consensus  A STKGP SVFP LAPS SKST SGGTAALGC LIVKDY FFEPVTV SWN SGALTSGVHT FPAVLQ SSGLY SLSSVVTVPSSSLGTQTY ICNVNHKPSNTKVDKKAEP Consensus  K SCDKTHTCPPCPAPELLGGP SVFLFPPKPKDT LM ISRTP EVTCVVVDVSH EDPEVKFNWYVDGVEVHNAKTKPR EEQYNSTYRVVSVLTVLHQDWLNGK Consensus  EYKCKVSNKALPAPIEKTISKAKGQPREPQVYTLPPSRDELTKNQVSLTCLVKGFYPSDIAVEWESNGQPENYKTTPPVLDSDGSFFLYSKLTVDKSRW 301
IgG1
IDEC-131
Parent 310    320    330    (SEQ ID NO: 11)
                       (SEQ ID NO: 12)
                       (SEQ ID NO: 13)

(SEQ ID NO:14)

Consensus  QQGNVFSC SVMHEALHNHYTQKSLSLSPGK    (SEQ ID NO:14)

FIG. 2A

(SEQ ID NO: 15)
(SEQ ID NO: 16)
(SEQ ID NO: 17)

(SEQ ID NO: 18)

IDEC-131
Parent
21-31

Consensus  EVQLQESGPGLVKPSETLSLTCTVSGDSITNGFWIRKPPGNKLEYMGYISYSGSTYYNPSLKSRISISRDTSKNQFSLKLSSVTAADTGVYTCAYRSYGRTPYYFDFWGQGTTLTVSS

Variable heavy-chain sequences

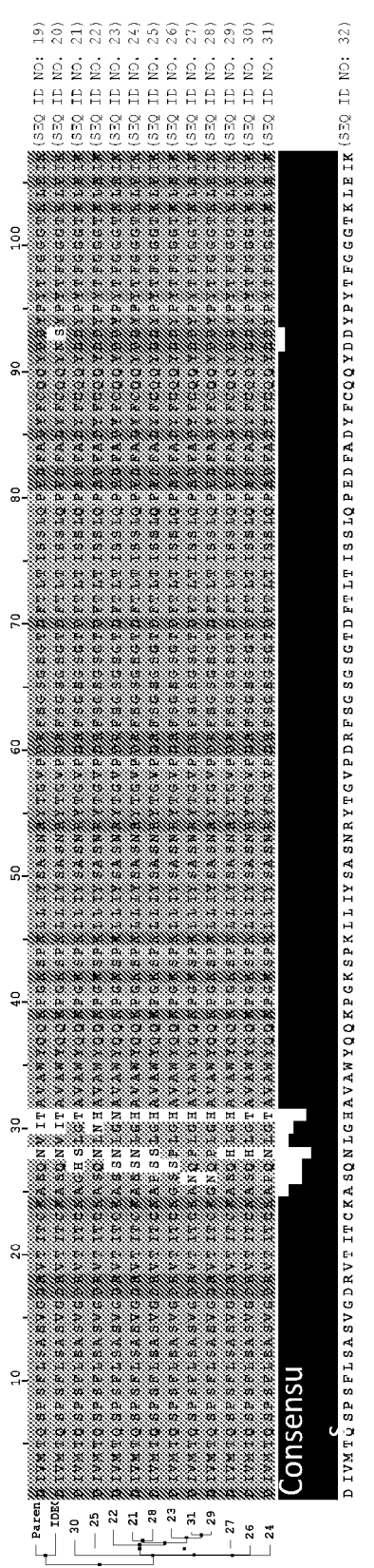
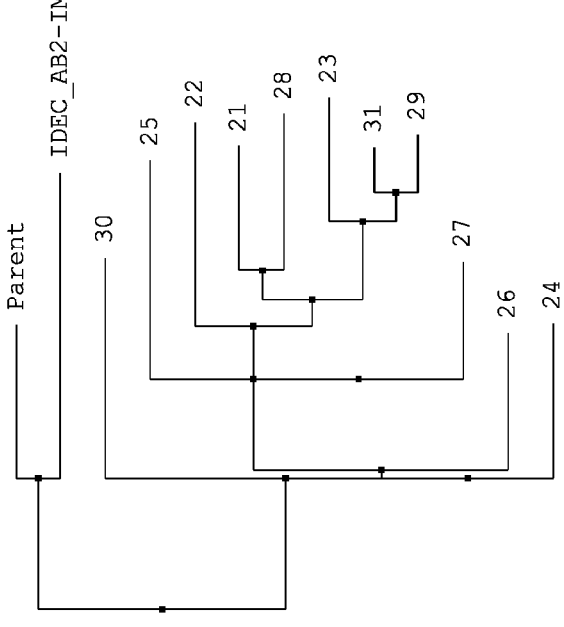
Variable light-chain sequences
FIG. 2C

Improved potency: using IDEC epitope

INX021 shows better binding
to CD40L on T cells

INX021 shows more potent
inhibition of T cell CD40L-driven B
cell activation

FcR mutants of hIgG anti-mCD40L induce tolerance

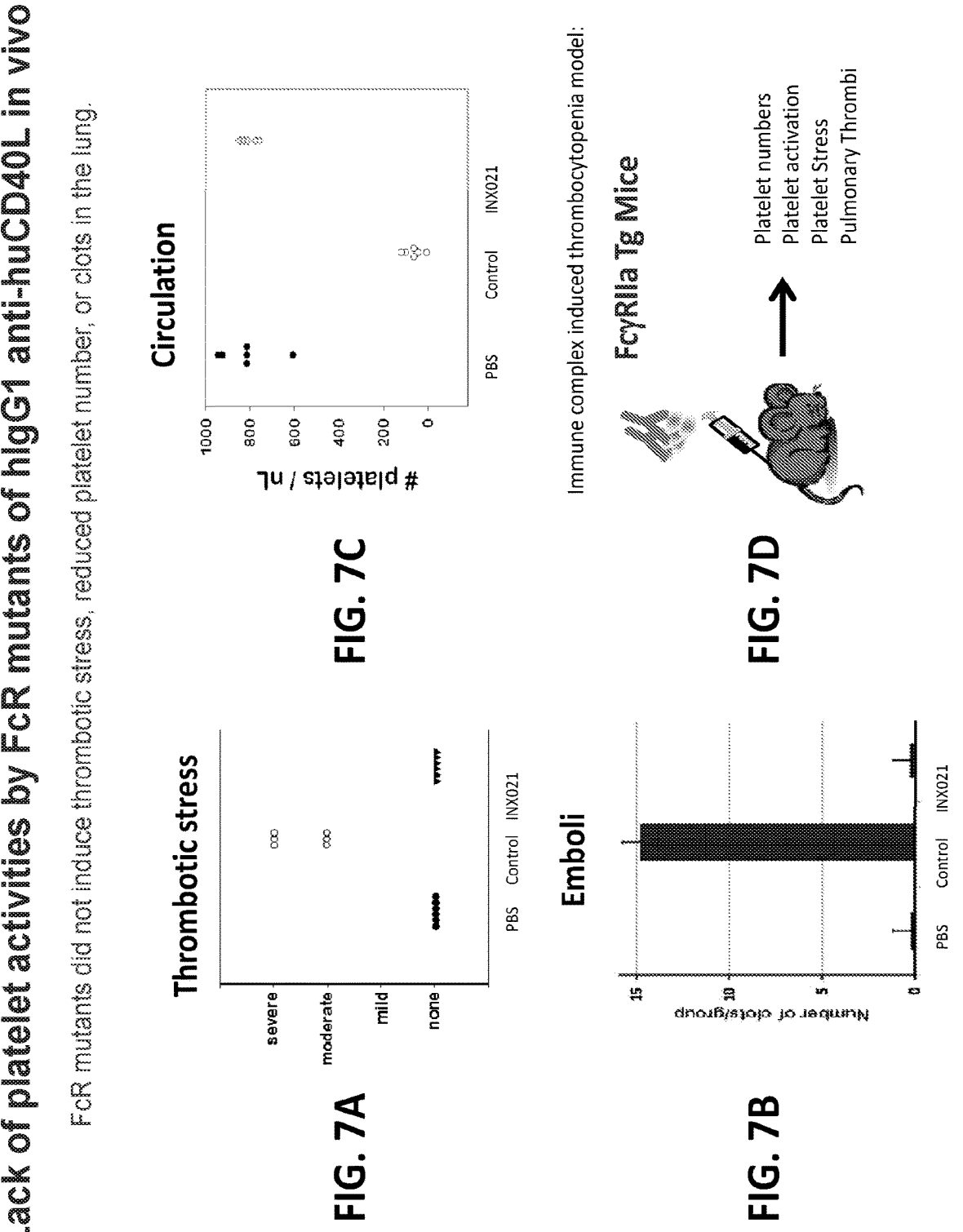

Activity of FcR/C1q mutant anti-mCD40L abs

FcR/C1q-binding mutants are still active in models of interest such as EAE, tolerance and immune response to MOG.

B cell expression of CD86

TDAR results: IgG TDAR (TOP) compared with saline controls (dotted line). IgM TDAR (bottom) compared with saline controls (dotted line).

Germinal Center scores (above): Number and degree of cellularity of the germinal centers in spleen and LN of treated animals.

TOP: Representative 5C8 histopathology of emboli.

Bottom: Representative histopathology of saline (left) and INX021 (right) emboli

FIGURE 12

Summary of lesion frequency compared with published UCB emboli data:

(CDP7657, an anti-CD40L antibody lacking an Fc domain, inhibits CD40L-dependent immune responses without thrombotic complications: an in vivo study Arthritis Res Ther. 2015; 17(1): 234.)

| Dose Group | Animals affected (%) | Total lung sections examined | Lung sections affected (%) |
|---|---|---|---|
| Historic Controls | | | |
| Saline | 7 (50%) | 406 | 2.5% |
| Biogen/UCB Pegylated Fab | | | |
| Saline | 1 (25%) | 116 | 0.9% |
| Peg-Fab CDP765 | 3 (37.5%) | 203 | 2.0% |
| Aglycosyl 5C8 | 3 (37.5%) | 232 | 1.3% |
| hu5C8 | 5 (62.5%) | 232 | 17.6% |
| | | | |
| ImmuNext INX021 | | | |
| Vehicle | 2 (50%) | 174 | 1.7% |
| INX021 | 3 (37.5%) | 232 | 3.4% |
| ch5C8 | 6 (75%) | 232 | 3.8% |

```
                            SEQUENCE LISTING

Sequence total quantity: 34
SEQ ID NO: 1              moltype = AA  length = 120
FEATURE                   Location/Qualifiers
REGION                    1..120
                          note = INX021 Variable Heavy
source                    1..120
                          mol_type = protein
                          organism = synthetic construct
SEQUENCE: 1
EVQLQESGPG LVKPSETLSL TCTVSGDSIT NGFWIWIRKP PGNKLEYMGY ISYSGSTYYN   60
PSLKSRISIS RDTSKNQFSL KLSSVTAADT GVYYCAYRSY GRTPYYFDYW GQGTTLTVSS  120

SEQ ID NO: 2              moltype = AA  length = 107
FEATURE                   Location/Qualifiers
REGION                    1..107
                          note = INX021 Variable Light
source                    1..107
                          mol_type = protein
                          organism = synthetic construct
SEQUENCE: 2
DIVMTQSPSF LSASVGDRVT ITCKASSNLG HAVAWYQQKP GKSPKLLIYS ASNRYTGVPD   60
RFSGSGSGTD FTLTISSLQP EDFADYFCQQ YDDYPYTFGG GTKLEIK               107

SEQ ID NO: 3              moltype = AA  length = 330
FEATURE                   Location/Qualifiers
REGION                    1..330
                          note = INX021 Constant Heavy
source                    1..330
                          mol_type = protein
                          organism = synthetic construct
SEQUENCE: 3
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKAEP KSCDKTHTCP PCPAPELLGG  120
PSVFLFPPKP KDTLMISRTP EVTCVVVDVS HRDPEVKFNW YVDGVEVHNA KTKPREEQYN  180
STYRVVSVLT VLHQDWLNGK EYKCAVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 4              moltype = AA  length = 107
FEATURE                   Location/Qualifiers
REGION                    1..107
                          note = INX021 Constant Light
source                    1..107
                          mol_type = protein
                          organism = synthetic construct
SEQUENCE: 4
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC               107

SEQ ID NO: 5              moltype = AA  length = 10
FEATURE                   Location/Qualifiers
```

-continued

```
source                    1..10
                          mol_type = protein
                          organism = Mus musculus
SEQUENCE: 5
GDSITNGFWI                                                              10

SEQ ID NO: 6              moltype = AA   length = 9
FEATURE                   Location/Qualifiers
source                    1..9
                          mol_type = protein
                          organism = Mus musculus
SEQUENCE: 6
YISYSGSTY                                                               9

SEQ ID NO: 7              moltype = AA   length = 13
FEATURE                   Location/Qualifiers
source                    1..13
                          mol_type = protein
                          organism = Mus musculus
SEQUENCE: 7
YRSYGRTPYY FDY                                                          13

SEQ ID NO: 8              moltype = AA   length = 11
FEATURE                   Location/Qualifiers
source                    1..11
                          mol_type = protein
                          organism = Mus musculus
SEQUENCE: 8
KASSNLGHAV A                                                            11

SEQ ID NO: 9              moltype = AA   length = 7
FEATURE                   Location/Qualifiers
source                    1..7
                          mol_type = protein
                          organism = Mus musculus
SEQUENCE: 9
SASNRYT                                                                 7

SEQ ID NO: 10            moltype = AA   length = 9
FEATURE                   Location/Qualifiers
source                    1..9
                          mol_type = protein
                          organism = Mus musculus
SEQUENCE: 10
QQYDDYPYT                                                               9

SEQ ID NO: 11            moltype = AA   length = 330
FEATURE                   Location/Qualifiers
source                    1..330
                          mol_type = protein
                          organism = Homo sapiens
SEQUENCE: 11
ASTKGPSVFP LAPSSKSTSG GTAALGCLVK DYFPEPVTVS WNSGALTSGV HTFPAVLQSS       60
GLYSLSSVVT VPSSSLGTQT YICNVNHKPS NTKVDKKVEP KSCDKTHTCP PCPAPELLGG       120
PSVFLFPPKP KDTLMISRTP EVTCVVVDVS HEDPEVKFNW YVDGVEVHNA KTKPREEQYN       180
STYRVVSVLT VLHQDWLNGK EYKCKVSNKA LPAPIEKTIS KAKGQPREPQ VYTLPPSRDE       240
LTKNQVSLTC LVKGFYPSDI AVEWESNGQP ENNYKTTPPV LDSDGSFFLY SKLTVDKSRW       300
QQGNVFSCSV MHEALHNHYT QKSLSLSPGK                                        330

SEQ ID NO: 12            moltype = AA   length = 330
FEATURE                   Location/Qualifiers
REGION                    1..330
                          note = IDEC-131
source                    1..330
                          mol_type = protein
                          organism = synthetic construct
SEQUENCE: 12
ASTKGPSVFP LAPSSKSTSG GTAALGCLVK DYFPEPVTVS WNSGALTSGV HTFPAVLQSS       60
GLYSLSSVVT VPSSSLGTQT YICNVNHKPS NTKVDKKVEP KSCDKTHTCP PCPAPELLGG       120
PSVFLFPPKP KDTLMISRTP EVTCVVVDVS HEDPEVKFNW YVDGVEVHNA KTKPREEQYN       180
STYRVVSVLT VLHQDWLNGK EYKCKVSNKA LPAPIEKTIS KAKGQPREPQ VYTLPPSRDE       240
LTKNQVSLTC LVKGFYPSDI AVEWESNGQP ENNYKTTPPV LDSDGSFFLY SKLTVDKSRW       300
QQGNVFSCSV MHEALHNHYT QKSLSLSPGK                                        330

SEQ ID NO: 13            moltype = AA   length = 330
FEATURE                   Location/Qualifiers
source                    1..330
                          mol_type = protein
                          organism = Mus musculus
```

```
SEQUENCE: 13
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKAEP KSCDKTHTCP PCPAPELLGG  120
PSVFLFPPKP KDTLMISRTP EVTCVVVDVS HRDPEVKFNW YVDGVEVHNA KTKPREEQYN  180
STYRVVSVLT VLHQDWLNGK EYKCAVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 14           moltype = AA   length = 330
FEATURE                 Location/Qualifiers
REGION                  1..330
                        note = Constant Heavy-Chain Sequence Consensus Sequence
source                  1..330
                        mol_type = protein
                        organism = synthetic construct SEQUENCE: 14
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 15           moltype = AA   length = 120
FEATURE                 Location/Qualifiers
REGION                  1..120
                        note = IDEC-131 Variable Heavy-Chain Sequence
source                  1..120
                        mol_type = protein
                        organism = synthetic construct
SEQUENCE: 15
EVQLQESGPG LVKPSETLSL TCTVSGDSIT NGFWIWIRKP PGNKLEYMGY ISYSGSTYYN   60
PSLKSRISIS RDTSKNQFSL KLSSVTAADT GVYYCACRSY GRTPYYFDFW GQGTTLTVSS  120

SEQ ID NO: 16           moltype = AA   length = 120
FEATURE                 Location/Qualifiers
source                  1..120
                        mol_type = protein
                        organism = Mus musculus
SEQUENCE: 16
EVQLQESGPG LVKPSETLSL TCTVSGDSIT NGFWIWIRKP PGNKLEYMGY ISYSGSTYYN   60
PSLKSRISIS RDTSKNQFSL KLSSVTAADT GVYYCAYRSY GRTPYYFDFW GQGTTLTVSS  120

SEQ ID NO: 17           moltype = AA   length = 120
FEATURE                 Location/Qualifiers
source                  1..120
                        mol_type = protein
                        organism = Homo sapiens
SEQUENCE: 17
EVQLQESGPG LVKPSETLSL TCTVSGDSIT NGFWIWIRKP PGNKLEYMGY ISYSGSTYYN   60
PSLKSRISIS RDTSKNQFSL KLSSVTAADT GVYYCAYRSY GRTPYYFDYW GQGTTLTVSS  120

SEQ ID NO: 18           moltype = AA   length = 120
FEATURE                 Location/Qualifiers
REGION                  1..120
                        note = Variable heavy-chain sequence consensus
source                  1..120
                        mol_type = protein
                        organism = synthetic construct
SEQUENCE: 18
EVQLQESGPG LVKPSETLSL TCTVSGDSIT NGFWIWIRKP PGNKLEYMGY ISYSGSTYYN   60
PSLKSRISIS RDTSKNQFSL KLSSVTAADT GVYYCAYRSY GRTPYYFDFW GQGTTLTVSS  120

SEQ ID NO: 19           moltype = AA   length = 107
FEATURE                 Location/Qualifiers
source                  1..107
                        mol_type = protein
                        organism = Mus musculus
SEQUENCE: 19
DIVMTQSPSF LSASVGDRVT ITCKASQNVI TAVAWYQQKP GKSPKLLIYS ASNRYTGVPD   60
RFSGSGSGTD FTLTISSLQP EDFADYFCQQ YDDYPYTFGG GTKLEIK                107

SEQ ID NO: 20           moltype = AA   length = 107
FEATURE                 Location/Qualifiers
REGION                  1..107
                        note = IDEC_AB2-IMX variable light chain sequence
source                  1..107
                        mol_type = protein
                        organism = synthetic construct
```

```
SEQUENCE: 20
DIVMTQSPSF LSASVGDRVT ITCKASQNVI TAVAWYQQKP GKSPKLLIYS ASNRYTGVPD    60
RFSGSGSGTD FTLTISSLQP EDFADYFCQQ YNSYPYTFGG GTKLEIK                  107

SEQ ID NO: 21              moltype = AA   length = 107
FEATURE                    Location/Qualifiers
REGION                     1..107
                           note = Variable light-chain sequence 30
source                     1..107
                           mol_type = protein
                           organism = synthetic construct
SEQUENCE: 21
DIVMTQSPSF LSASVGDRVT ITCKAGHSLG TAVAWYQQKP GKSPKLLIYS ASNRYTGVPD    60
RFSGSGSGTD FTLTISSLQP EDFADYFCQQ YDDYPYTFGG GTKLEIK                  107

SEQ ID NO: 22              moltype = AA   length = 107
FEATURE                    Location/Qualifiers
REGION                     1..107
                           note = Variable light-chain sequence 25
source                     1..107
                           mol_type = protein
                           organism = synthetic construct
SEQUENCE: 22
DIVMTQSPSF LSASVGDRVT ITCKASQNLN HAVAWYQQKP GKSPKLLIYS ASNRYTGVPD    60
RFSGSGSGTD FTLTISSLQP EDFADYFCQQ YDDYPYTFGG GTKLEIK                  107

SEQ ID NO: 23              moltype = AA   length = 107
FEATURE                    Location/Qualifiers
REGION                     1..107
                           note = Variable light-chain sequence 22
source                     1..107
                           mol_type = protein
                           organism = synthetic construct
SEQUENCE: 23
DIVMTQSPSF LSASVGDRVT ITCKASSNLG NAVAWYQQKP GKSPKLLIYS ASNRYTGVPD    60
RFSGSGSGTD FTLTISSLQP EDFADYFCQQ YDDYPYTFGG GTKLEIK                  107

SEQ ID NO: 24              moltype = AA   length = 107
FEATURE                    Location/Qualifiers
REGION                     1..107
                           note = Variable light-chain sequence 21
source                     1..107
                           mol_type = protein
                           organism = synthetic construct
SEQUENCE: 24
DIVMTQSPSF LSASVGDRVT ITCKASSNLG HAVAWYQQKP GKSPKLLIYS ASNRYTGVPD    60
RFSGSGSGTD FTLTISSLQP EDFADYFCQQ YDDYPYTFGG GTKLEIK                  107

SEQ ID NO: 25              moltype = AA   length = 107
FEATURE                    Location/Qualifiers
REGION                     1..107
                           note = Variable light-chain sequence 28
source                     1..107
                           mol_type = protein
                           organism = synthetic construct
SEQUENCE: 25
DIVMTQSPSF LSASVGDRVT ITCKAPSSLG HAVAWYQQKP GKSPKLLIYS ASNRYTGVPD    60
RFSGSGSGTD FTLTISSLQP EDFADYFCQQ YDDYPYTFGG GTKLEIK                  107

SEQ ID NO: 26              moltype = AA   length = 107
FEATURE                    Location/Qualifiers
REGION                     1..107
                           note = Variable light-chain sequence 23
source                     1..107
                           mol_type = protein
                           organism = synthetic construct
SEQUENCE: 26
DIVMTQSPSF LSASVGDRVT ITCKGSSPLG HAVAWYQQKP GKSPKLLIYS ASNRYTGVPD    60
RFSGSGSGTD FTLTISSLQP EDFADYFCQQ YDDYPYTFGG GTKLEIK                  107

SEQ ID NO: 27              moltype = AA   length = 107
FEATURE                    Location/Qualifiers
REGION                     1..107
                           note = Variable light-chain sequence 31
source                     1..107
                           mol_type = protein
                           organism = synthetic construct
SEQUENCE: 27
DIVMTQSPSF LSASVGDRVT ITCKANQPLG HAVAWYQQKP GKSPKLLIYS ASNRYTGVPD    60
```

```
RFSGSGSGTD FTLTISSLQP EDFADYFCQQ YDDYPYTFGG GTKLEIK                    107

SEQ ID NO: 28              moltype = AA   length = 107
FEATURE                    Location/Qualifiers
REGION                     1..107
                           note = Variable light-chain sequence 29
source                     1..107
                           mol_type = protein
                           organism = synthetic construct
SEQUENCE: 28
DIVMTQSPSF LSASVGDRVT ITCKGNQPLG HAVAWYQQKP GKSPKLLIYS ASNRYTGVPD    60
RFSGSGSGTD FTLTISSLQP EDFADYFCQQ YDDYPYTFGG GTKLEIK                    107

SEQ ID NO: 29              moltype = AA   length = 107
FEATURE                    Location/Qualifiers
REGION                     1..107
                           note = Variable light-chain sequence 27
source                     1..107
                           mol_type = protein
                           organism = synthetic construct
SEQUENCE: 29
DIVMTQSPSF LSASVGDRVT ITCKASQHLG HAVAWYQQKP GKSPKLLIYS ASNRYTGVPD    60
RFSGSGSGTD FTLTISSLQP EDFADYFCQQ YDDYPYTFGG GTKLEIK                    107

SEQ ID NO: 30              moltype = AA   length = 107
FEATURE                    Location/Qualifiers
REGION                     1..107
                           note = Variable light-chain sequence 26
source                     1..107
                           mol_type = protein
                           organism = synthetic construct
SEQUENCE: 30
DIVMTQSPSF LSASVGDRVT ITCKASQHLG TAVAWYQQKP GKSPKLLIYS ASNRYTGVPD    60
RFSGSGSGTD FTLTISSLQP EDFADYFCQQ YDDYPYTFGG GTKLEIK                    107

SEQ ID NO: 31              moltype = AA   length = 107
FEATURE                    Location/Qualifiers
REGION                     1..107
                           note = Variable light-chain sequence 24
source                     1..107
                           mol_type = protein
                           organism = synthetic construct
SEQUENCE: 31
DIVMTQSPSF LSASVGDRVT ITCKAPQNLG TAVAWYQQKP GKSPKLLIYS ASNRYTGVPD    60
RFSGSGSGTD FTLTISSLQP EDFADYFCQQ YDDYPYTFGG GTKLEIK                    107

SEQ ID NO: 32              moltype = AA   length = 107
FEATURE                    Location/Qualifiers
REGION                     1..107
                           note = Variable light-chain sequence consensus
source                     1..107
                           mol_type = protein
                           organism = synthetic construct
SEQUENCE: 32
DIVMTQSPSF LSASVGDRVT ITCKASQNLG HAVAWYQQKP GKSPKLLIYS ASNRYTGVPD    60
RFSGSGSGTD FTLTISSLQP EDFADYFCQQ YDDYPYTFGG GTKLEIK                    107

SEQ ID NO: 33              moltype = AA   length = 460
FEATURE                    Location/Qualifiers
REGION                     1..460
                           note = Heavy Chain
source                     1..460
                           mol_type = protein
                           organism = synthetic construct
SEQUENCE: 33
EVQLQESGPG LVKPSETLSL TCTVSGDSIT NGFWIWIRKP PGNKLEYMGY ISYSGSTYYN    60
PSLKSRISIS RDTSKNQFSL KLSSVTAADT GVYYCAYRSY GRTPYYFDYW GQGTTLTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKAEP KSCDKTHTCP PCPAPELLGG    240
PSVFLFPPKP KDTLMISRTP EVTCVVVDVS HRDPEVKFNW YVDGVEVHNA KTKPREEQYN    300
STYRVVSVLT VLHQDWLNGK EYKCAVSNKA LPAPIEKTIS KAKGQPREPQ VYTLPPSRDE    360
LTKNQVSLTC LVKGFYPSDI LVKGFYPSDI AVEWESNGQP ENNYKTTPPV LDSDGSFFLY    420
SKLTVDKSRW QQGNVFSCSV MHEALHNHYT QKSLSLSPGK                          460

SEQ ID NO: 34              moltype = AA   length = 214
FEATURE                    Location/Qualifiers
REGION                     1..214
                           note = Light Chain
source                     1..214
```

-continued

```
                        mol_type = protein
                        organism = synthetic construct
SEQUENCE: 34
DIVMTQSPSF LSASVGDRVT ITCKASSNLG HAVAWYQQKP GKSPKLLIYS ASNRYTGVPD   60
RFSGSGSGTD FTLTISSLQP EDFADYFCQQ YDDYPYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

ANTI-CD154 ANTIBODY HAVING IMPROVED BINDING, FUNCTIONAL AND SAFETY CHARACTERISTICS AND USE IN HUMAN IMMUNOTHERAPY

RELATED APPLICATIONS

This application is a divisional of U.S. patent application Ser. No. 17/101,139, filed Nov. 23, 2020, now U.S. Pat. No. 11,596,689, which is a divisional of U.S. patent application Ser. No. 15/744,379, filed Jan. 12, 2018, now U.S. Pat. No. 10,874,738, which is a U.S. national phase application of Int'l. Appl. No. PCT/US2016/042074, filed Jul. 13, 2016, which claims priority to Provisional Appl. No. 62/277,201, filed Jan. 11, 2016, Provisional Appl. No. 62/197,966, filed Jul. 28, 2015, and Provisional Appl. No. 62/192,269, filed Jul. 14, 2015, the disclosures of each of which are hereby incorporated by reference in their entireties.

GOVERNMENT SUPPORT CLAUSE

This invention was made with government support under Grant/Contract Number(s) R44 AI098261 awarded by the National Institutes of Health. The government has certain rights in the invention.

REFERENCE TO AN ELECTRONIC SEQUENCE LISTING

The contents of the electronic sequence listing (1143260.002603.xml; Size: 43,788 bytes; and Date of Creation: Jan. 31, 2023) is herein incorporated by reference in its entirety.

BACKGROUND

Field of the Invention

The present invention relates to improved anti-CD154 (CD154) antibodies having reduced toxicity and functional properties and their use in immune therapies, especially the treatment of inflammatory disorders, allergy, autoimmunity, transplant, and cancers. In particular the invention provides high affinity anti-CD154 antibodies with improved affinity and functional activity which do not elicit thrombogenic or clotting reactions in vivo, and which elicit desired therapeutic properties such as the induction of immune tolerance and the blockade of humoral immunity.

Field of the Invention

The present invention relates to improved anti-CD154 (CD154) antibodies having reduced toxicity and functional properties and their use in immune therapies, especially the treatment of inflammatory disorders, allergy, autoimmunity, transplant, and cancers. In particular the invention provides high affinity anti-CD154 antibodies with improved affinity and functional activity which do not elicit thrombogenic or clotting reactions in vivo, and which elicit desired therapeutic properties such as the induction of immune tolerance and the blockade of humoral immunity.

Description of Related Art

CD40L (CD154) is a highly validated and valuable therapeutic target in autoimmunity, graft rejection and other immune-related diseases in mice, non-human primates (NHP) and humans. In numerous Phase II Clinical Trials, UCD154 has been shown to effectively block the activities of CD154 in vivo and ameliorate disease. αCD154 is distinct from all other therapeutics in its impact on the immune response; it is one of the only therapeutics that can induce functional immunological tolerance, as demonstrated both in mice and monkeys. In mice, virtually all autoimmune disease models can be effectively ameliorated with αCD154 therapy (Noelle, R. J., Mackey, M., Foy, T., Buhlmann, J. and Burns, C., "CD40 and its ligand in autoimmunity". *Ann N Y Acad Sci* 1997. 815: 384-391; Mackey, M. F., Barth, R. J., Jr. and Noelle, R. J., "The role of CD40/CD154 interactions in the priming, differentiation, and effector function of helper and cytotoxic T cells", *J Leukoc Biol* 1998. 63: 418-428; Noelle, R. J., "CD40 and its ligand in cell-mediated immunity". *Agents Actions Suppl* 1998. 49: 17-22; and Quezada, S. A., Jarvinen, L. Z., Lind, E. F. and Noelle, R. J., "CD40/CD154 Interactions at the Interface of Tolerance and Immunity". *Annu Rev Immunol* 2004. 22: 307-328), with long-term remission observed.

In NHP, permanent allograft tolerance can be achieved using short courses of treatments comprised of αCD154 (Kenyon, N. S., Chatzipetrou, M., Masetti, M., Ranuncoli, A., Oliveira, M., Wagner, J. L., Kirk, A. D., Harlan, D. M., Burkly, L. C. and Ricordi, C., "Long-term survival and function of intrahepatic islet allografts in rhesus monkeys treated with humanized anti-CD154". *Proc Natl Acad Sci., USA* 1999. 96: 8132-8137; Kirk, A. D., Burkly, L. C., Batty, D. S., Baumgartner, R. E., Beming, J. D., Buchanan, K., Fechner, J. H., Jr., Germond, R. L., Kampen, R. L., Patterson, N. B., Swanson, S. J., Tadaki, D. K., TenHoor, C. N., White, L., Knechtle, S. J. and Harlan, D. M., "Treatment with humanized monoclonal antibody against CD154 prevents acute renal allograft rejection in nonhuman primates". *Nat Med* 1999. 5: 686-693).

Also, Phase II Clinical Trials in humans have indicated that αCD154 is effective in SLE (Sidiropoulos, P. I. and Boumpas, D. T., "Lessons learned from anti-CD154 treatment in systemic lupus erythematosus patients", *Lupus* 2004. 13: 391-397), Multiple Sclerosis (see preliminary data) and idiopathic thrombocytopenia (Sidiropoulos, P. I. and Boumpas, D. T., "Lessons learned from anti-CD154 treatment in systemic lupus erythematosus patients", *Lupus* 2004. 13: 391-397). As such, αCD154 is a unique drug that allows for short-term intervention with long-term clinical benefit. Its failures have not been in efficacy, but due to an unanticipated toxicity.

In the early 1990's IDEC Pharmaceuticals and Biogen Inc. (now Biogen Idec) launched two different αCD154 mAbs into multiple Phase I/II Clinical Trials. The antibody developed by IDEC (IDEC-131) was a humanized IgG1 derived from a murine anti-human CD154 antibody developed at Dartmouth College. This antibody and humanized variants are disclosed in U.S. Pat. Nos. 6,001,358; 6,440, 418; 6,506,383; 7,074,406; and 7,122,187, the contents of which are al incorporated by reference herein. While early indications demonstrated that the drug was highly effective, toxicity of another anti-CD154 prohibited continued clinical development. In the trials, the observed toxicity included the induction of thromboembolic events in patients. Based on toxicity concerns, all trials were suspended and efforts were directed towards re-engineering the mAbs to sustain efficacy and reduce toxicity.

While reduced toxicity has been achieved, there has been a substantial decrease in efficacy and the tolerance-inducing capacity of αCD154 mAbs (Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., "The contribution of Fc effector mechanisms in the efficacy of anti-CD154 immunotherapy depends on the nature of the immune challenge". *Int Immunol* 2004. 16: 1583-1594).

Biogen-Idec and UCB recently reported the development of anti-CD154 antibodies of reportedly improved safety. Specifically they reported producing a Pegylated anti-human CD154 Fab called CDP-7657 or ruplizumab. Because Fabs typically have very short in vivo half-life (i.e., about 4-8 hours) this Fab was to improve its pharmacokinetic properties. However, while reportedly clinically effective this antibody reportedly exhibits low potency. Also, Bristol Meyers Squib has reported the development of a domain antibody-Fc fusion protein comprising specificity to CD154. Reportedly this fusion protein has shown efficacy in mouse disease models, particularly the KLH challenge model and NZBxNZW SLE (lupus) model.

Notwithstanding the foregoing, there is still a significant need in the art for improved anti-CD154 antibodies, i.e., those which are both safe and effective, and which comprise good potency and pharmacokinetic properties. This invention attains these goals.

DETAILED DESCRIPTION OF THE FIGURES

FIGS. 1A-1C contain the amino acid sequences of an inventive anti-CD154 antibody which was derived from IDEC-131. In FIGS. 1A and 1B, the heavy chain and light chain polypeptides are shown (SEQ ID NOs: 33 and 34, respectively), wherein the variable regions contained in the heavy chain and light chain polypeptides are shown in bold, the affinity maturation mutated residues are underlined, and the Fc mutations are underlined. FIG. 1C shows the amino acid sequences of the VH and VL polypeptides (SEQ ID NOs: 1 and 2, respectively), the amino acid sequences of the constant heavy chain and constant light chain polypeptides (SEQ ID NOs: 3 and 4, respectively), and the amino acid sequences the CDRs (SEQ ID NOs: 5-10).

FIGS. 2A-2C aligns different modified IgG1 constant regions and modified light and heavy chain sequences derived from IDEC-131 and its parent murine antibody.

Figure 3:
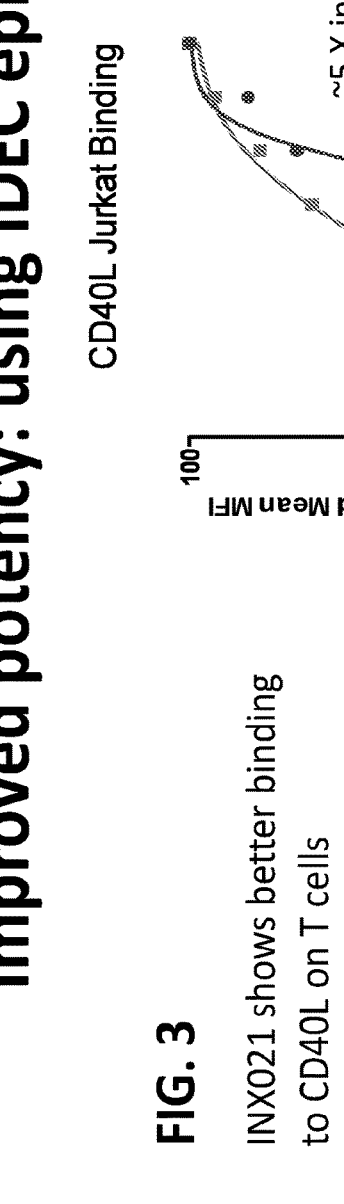

FIG. 3 contains the results of BIAcore binding assays comparing the binding of the inventive humanized anti-human CD154 antibody (referred to in the Figure and in this application as "INX021") to IDEC-131 for their ability to bind CD154 expressing Jurkat cells. As shown, the inventive antibody has about a 5-fold increase in binding affinity for CD154 (expressed on Jurkat cells) compared to IDEC-131.

Figure 4:
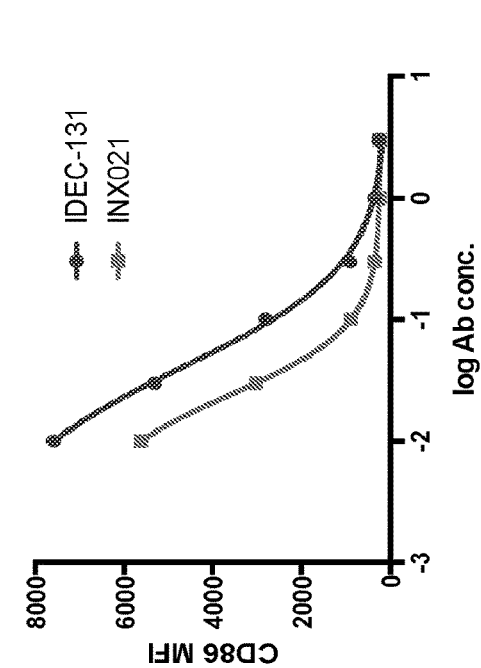

FIG. 4 contains experimental results showing that the inventive antibody ("INX021") more potently drives T cell CD154-driven B cell activation than IDEC-131.

Figure 5:
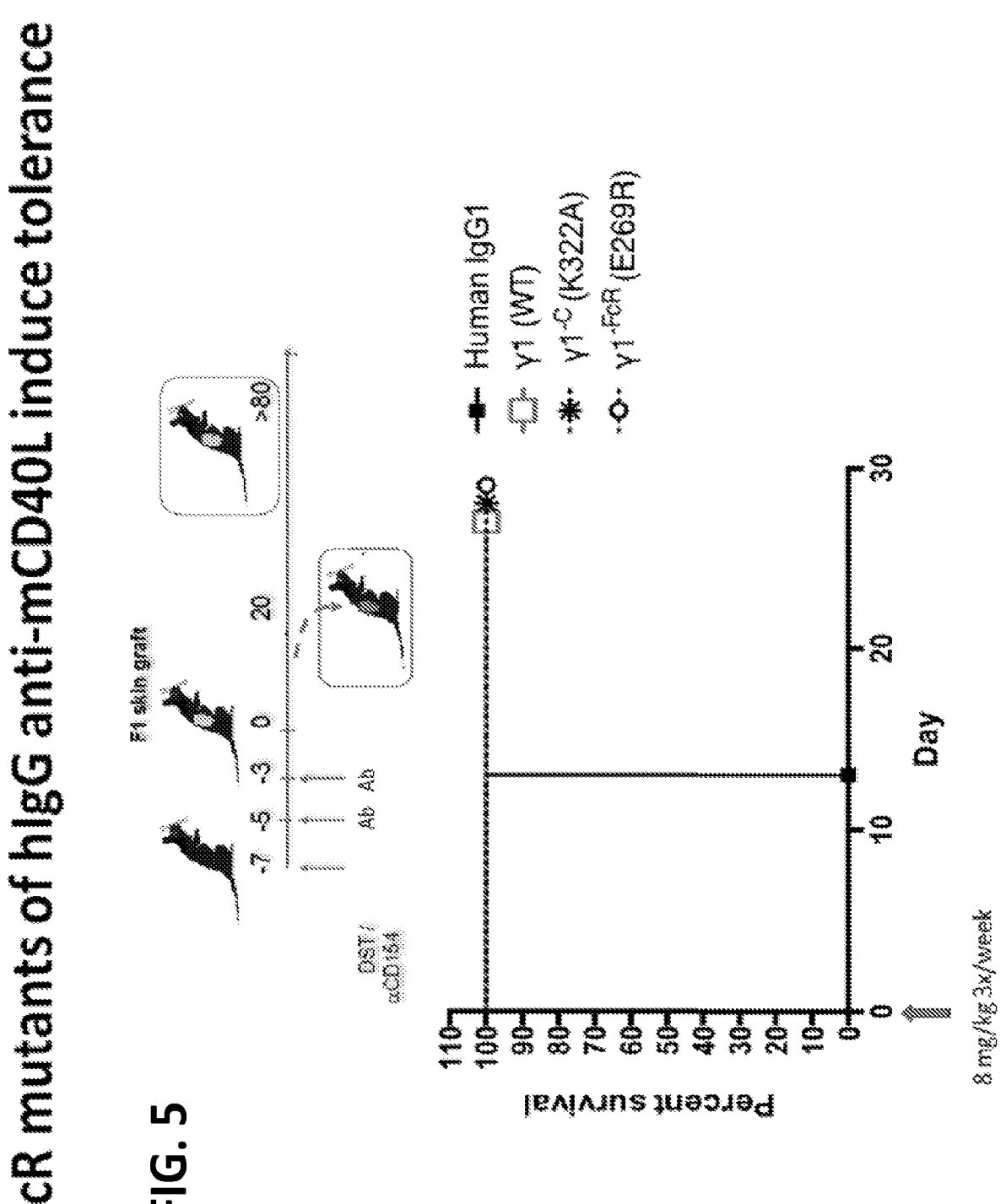

FIG. 5 contains experimental results showing that FcR mutants of human IgG anti-murine CD154 antibodies containing the same mutations as INX021 (K322A and E269R) induce tolerance in a skin tolerance model.

Figure 6:
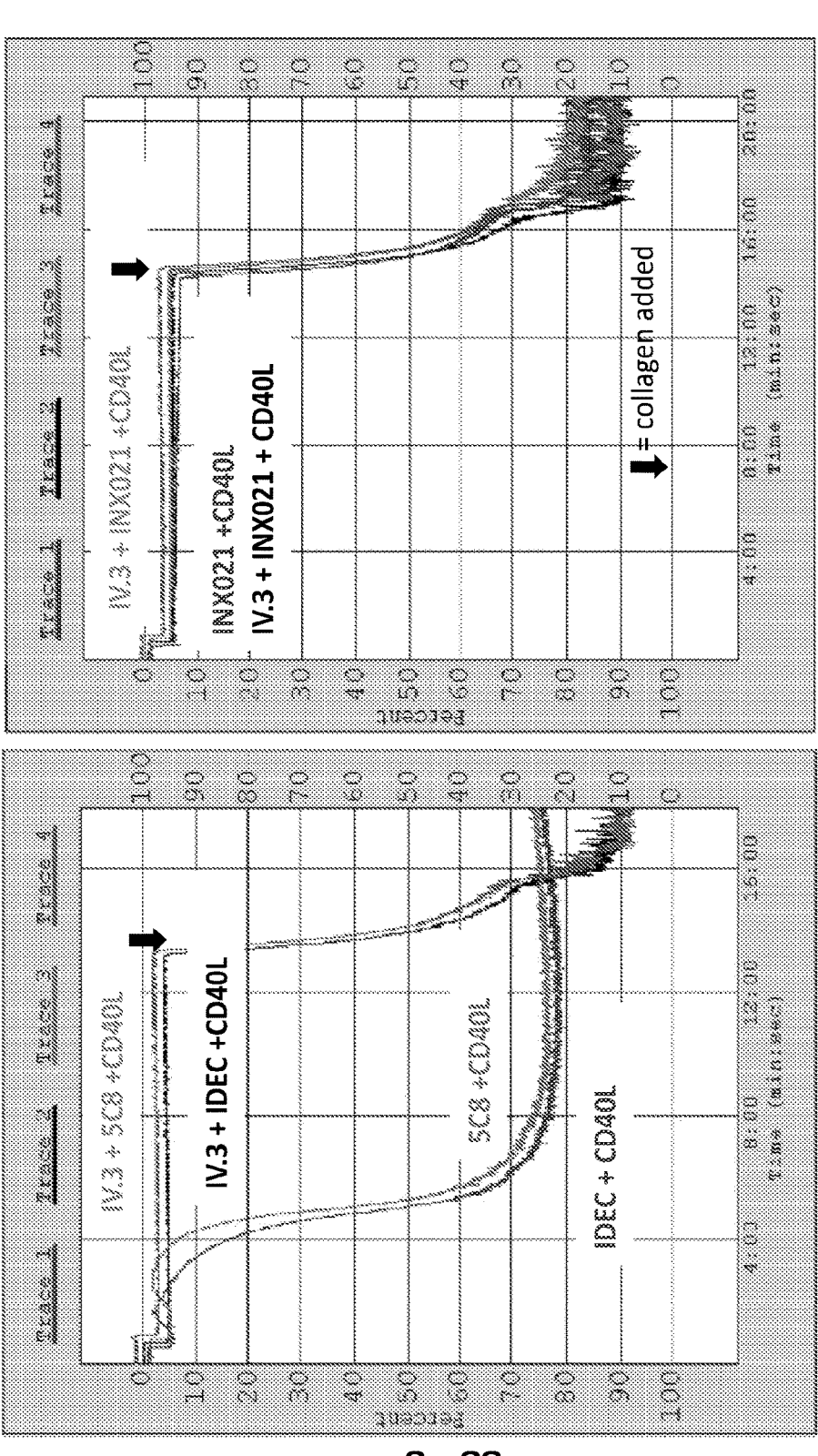

FIG. 6 contains experimental results showing that immune complexes of INX201 do not induce the aggregation or activation of mouse or human platelets in vitro.

FIGS. 7A-7D contains experimental results showing that INX021 does not elicit platelet activation or other effects on platelets compared to a positive control antibody. FIG. 7A shows it does not elicit thrombotic stress, FIG. 7B shows that it does not cause platelet aggregation or clotting as evidenced by no observed lung emboli, FIG. 7C shows that it does not affect the number of circulating platelets and FIG.

7D summarizes the observed advantages of this antibody observed in FcγRIIa Tg mice.

Figures 8A, 8B:
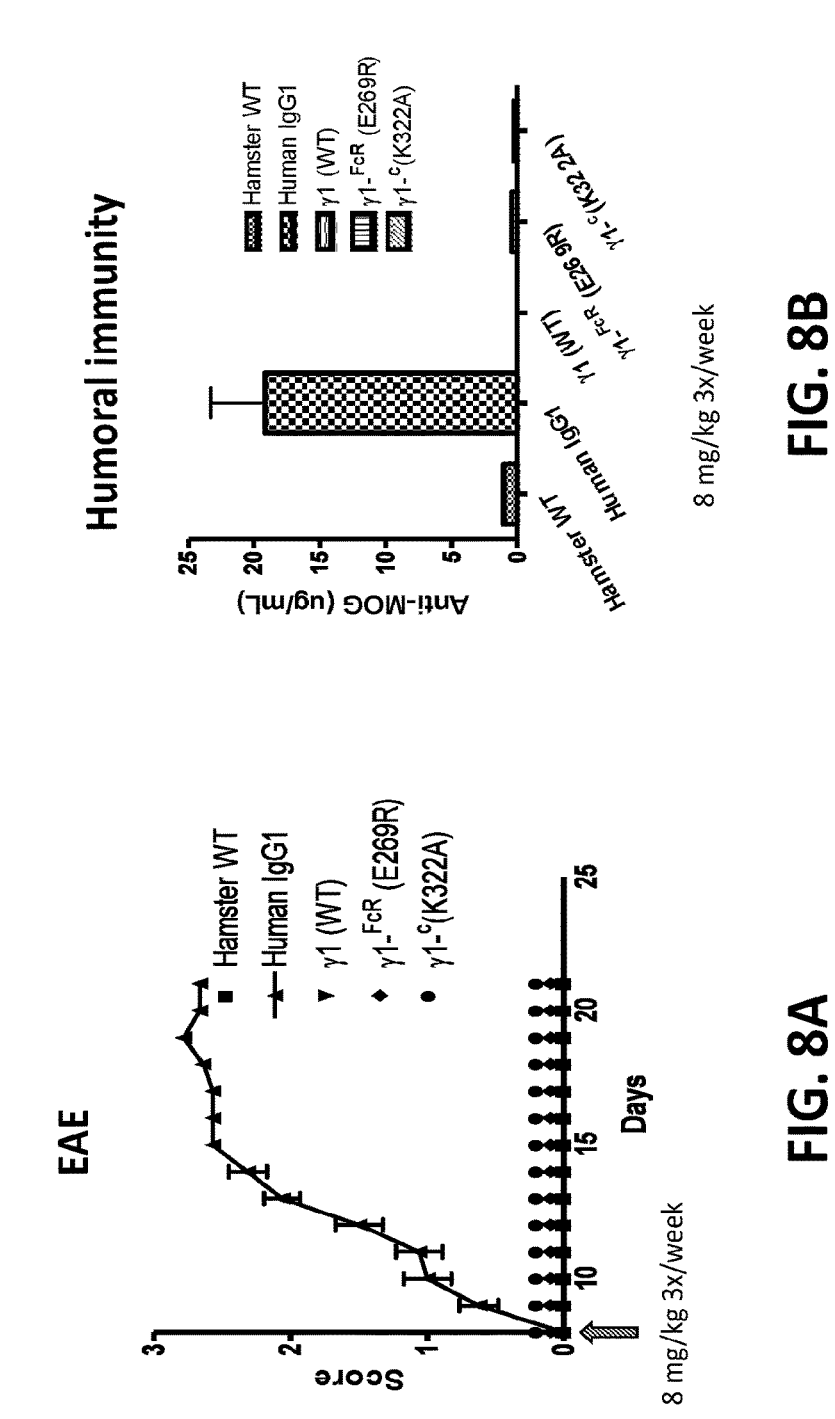

FIGS. 8A and 8B shows that anti-mouse CD154 IgG1 antibodies containing Fc mutations which reduce or eliminate FcR binding and complement activity (E2669R and K322A mutations contained in INX021) are immunosuppressive in animal models. FIG. 8A shows that an anti-CD154 antibody containing these mutations suppresses EAE and FIG. 8B shows that an anti-CD154 antibody containing these mutations suppresses humoral immunity and induce tolerance in response to myelin/oligodendrocyte glycoprotein ("MOG").

Figure 9:
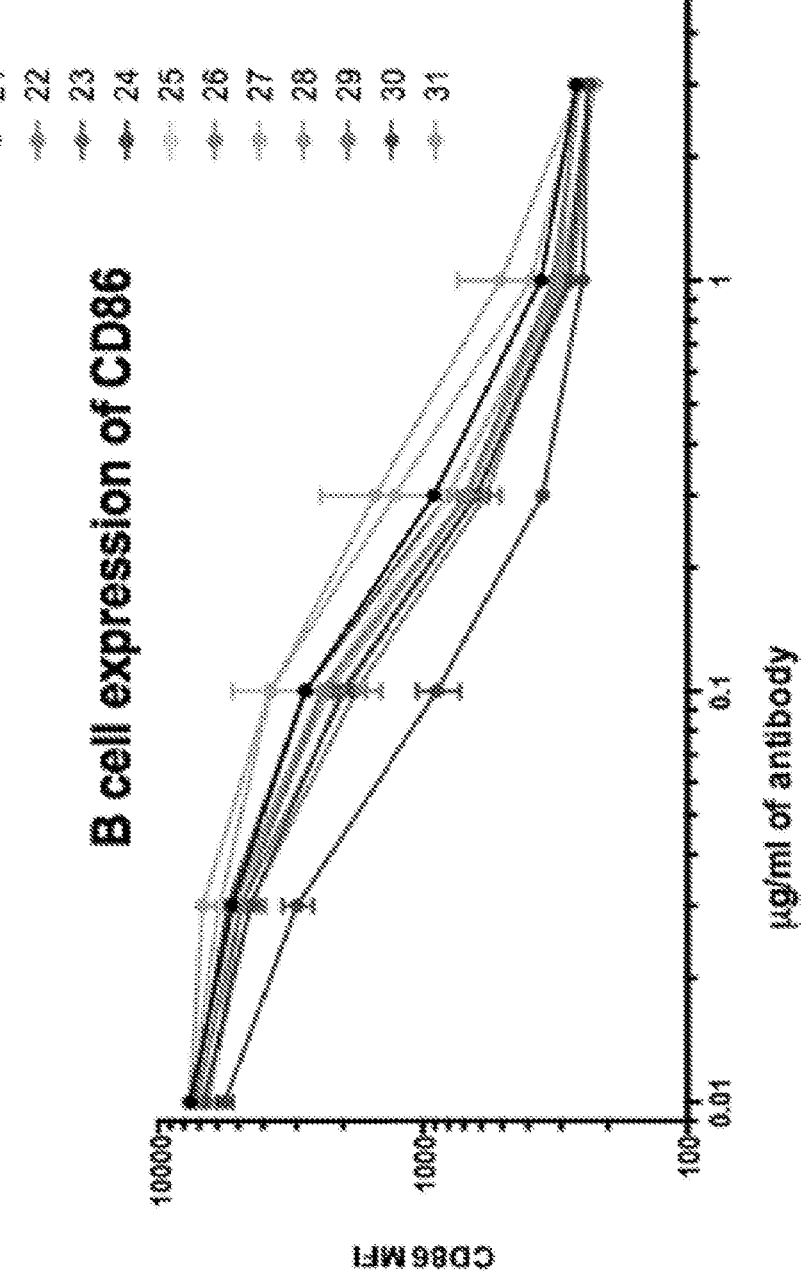

FIG. 9 compares the effects of different antibody variants of IDEC-131 including INX021 on T cell-induced B cell activation based on CD86 expression. The effects thereof are variable indicating that increased binding affinity does not necessarily correlate to better potency, i.e., immunosuppressant activity.

Figure 10A:
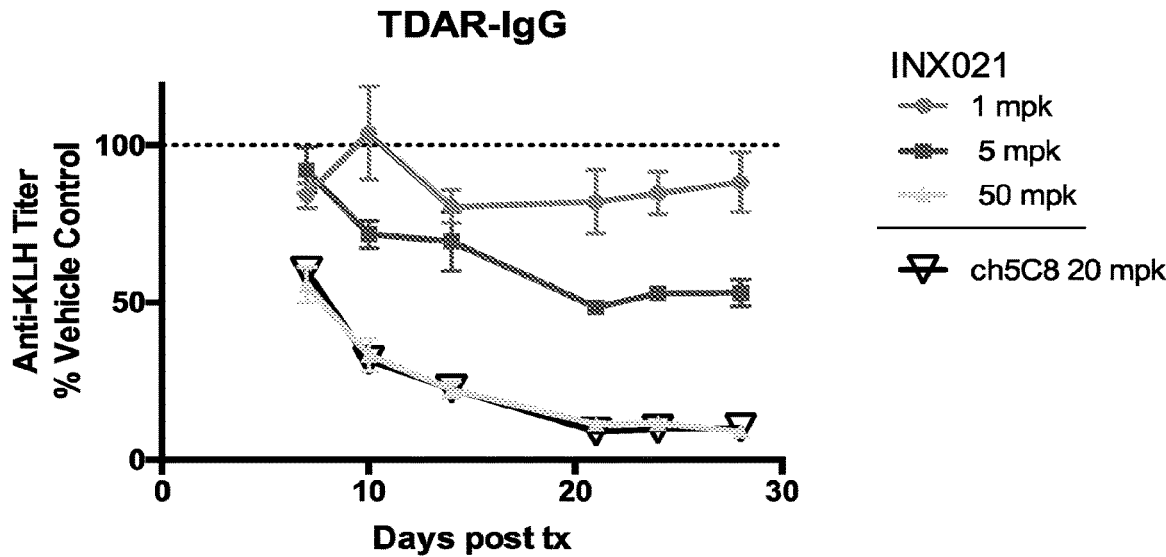
Figure 10B:
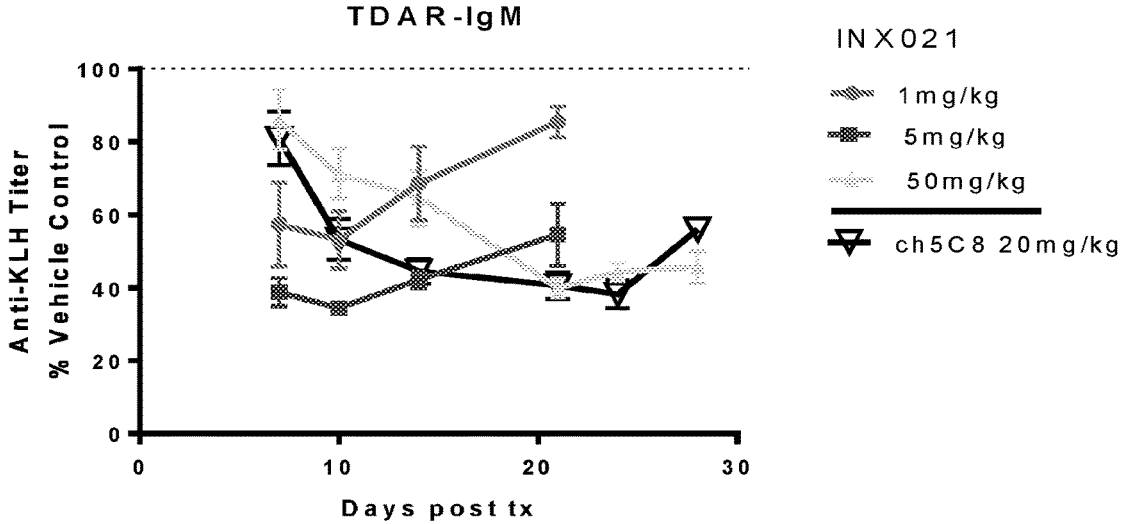

FIGS. 10A and 10B compares the effects of INX021 and chimeric 5c8 antibody on the production of IgG and IgM antibodies in a KLH assay. FIG. 10A compares their effects on IgG's and FIG. 10B compares their effects on IgM's.

Figure 11A:
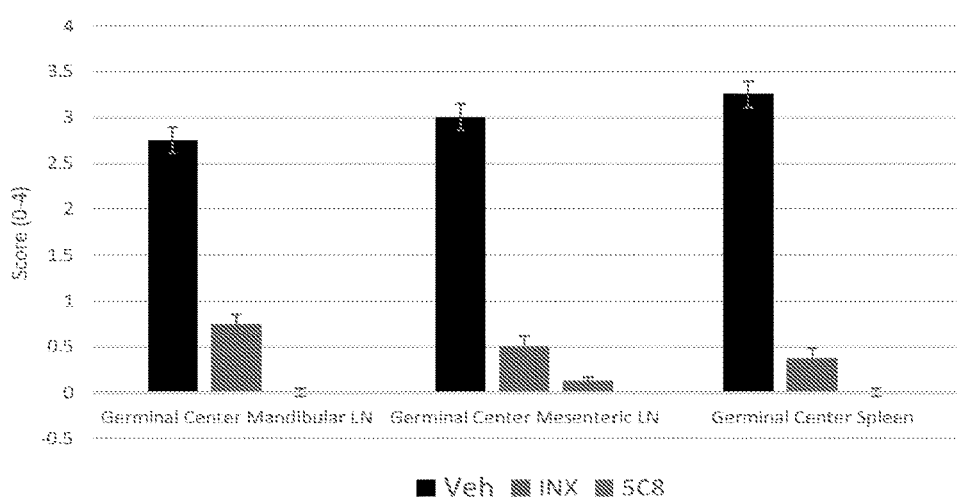
Figure 11B:
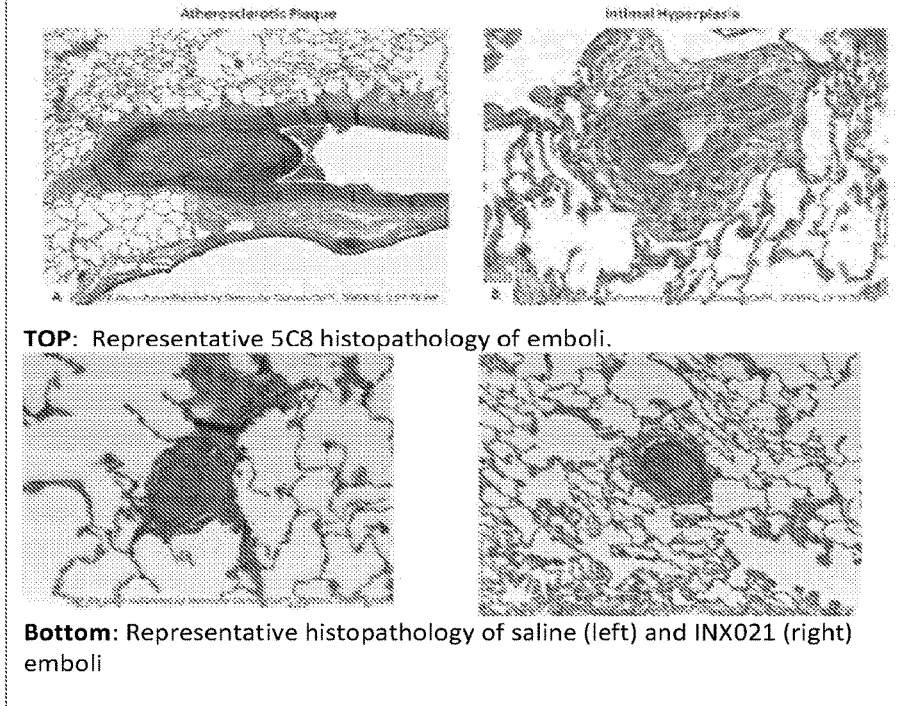

FIGS. 11A and 11B compares the effects of vehicle, INX021 and 5c8 antibody on germinal center scores. FIG. 11A shows the germinal score comparison and FIG. 11B contains histograms comparing number and degree of cellularity of the germinal centers in spleens and lymph nodes (LNs) of treated animals.

FIG. 12 summarizes the observed lesion frequency to published results with another anti-CD154 antibody (Pegylated αCD154 Fab of Biogen/UCB).

OBJECTS OF THE INVENTION

It is an object of the invention to provide an anti-CD154 antibody having improved efficacy, safety and pharmacokinetics for use in human therapy.

More specifically it is an object of the invention to provide a humanized anti-human CD154 antibody that comprises (i) a variable heavy polypeptide comprising or consisting of a polypeptide having a sequence selected from SEQ ID NO: 15, 17 and 18 shown in FIGS. 2A-2C, and (ii) and a variable light polypeptide comprising or consisting of a polypeptide having a sequence selected from SEQ ID NO: 20, 21, 22, 23, 24, 25, 26, 27, 28, 29, 30 and 31 shown in in FIGS. 2A-2C, with the proviso that the humanized anti-human CD154 antibody does not comprise the variable heavy polypeptide of SEQ ID NO:15 and the variable light polypeptide of SEQ ID NO:20.

Also, it is an object of the invention to provide a humanized anti-human CD154 antibody that comprises (i) a variable heavy polypeptide comprising or consisting of a polypeptide having the sequence of SEQ ID NO: 1 as shown in FIGS. 1A-C, and (ii) and a variable light polypeptide comprising or consisting of a polypeptide having the sequence of SEQ ID NO: 2 shown in FIGS. 1A-C.

Also it is an object of the invention to provide an anti-human CD154 antibody as set forth in the prior 3 paragraphs which comprises IgG1, IG2, IgG3 or IgG4 constant regions lacking the ability to bind C1Q and to bind to FcγR2 and/or FcγR3.

Also it is an object of the invention to provide an anti-human CD154 antibody as set forth in the prior 4 paragraphs which comprises which comprises human IgG1 constant regions lacking the ability to bind C1Q and to bind to FcRγ2 and/or FcRγ3.

Also it is an object of the invention to provide an anti-human CD154 antibody as set forth in the prior 5 paragraphs comprising human IgG1 constant regions comprising E269R and K322A mutations (numbering according to Kabat).

Also it is an object of the invention to provide a humanized anti-human CD154 antibody according to any of the prior paragraphs that comprises the IgG1 light and heavy constant regions of SEQ ID NO:3 and SEQ ID NO:2 shown in FIGS. 1A-C.

Also it is an object of the invention to provide a humanized anti-human CD154 antibody according to any of the prior paragraphs, wherein the antibody is of the IgG1 isotype and the Fc region of the antibody is further mutated to introduce at least one other mutation that affects effector function such as a mutation which impairs FcRn binding, one which impairs or eliminates glycosylation or another mutation which impairs the ability of the antibody to bind to an FcR such as FcγR2 or FcγR3 or another FcR or which impairs binding to complement.

Also it is an object of the invention to provide a humanized anti-human CD154 antibody according to any of the prior paragraphs, wherein the antibody is of the IgG1 isotype and the Fc region of the antibody is mutated to further introduce a E233P and/or a D265A mutation or any of the Fc mutations identified in Table 1, 2 or 3.

Also it is an object of the invention to provide a humanized anti-human CD154 antibody according to any of the prior paragraphs, wherein the antibody is of the IgG1 isotype and the Fc region of the antibody is mutated to introduce an E233P mutation.

Also it is an object of the invention to provide a humanized anti-human CD154 antibody according to any of the prior paragraphs, wherein the Fc region of the antibody is further mutated to introduce one or more other mutations that improve in vivo half-life.

Also it is an object of the invention to provide a pharmaceutical composition comprising a therapeutically or prophylactically effective amount of at least one humanized anti-human CD154 antibody according to any of the prior paragraphs.

Also it is an object of the invention to provide a pharmaceutical composition comprising a therapeutically or prophylactically effective amount of at least one humanized anti-human CD154 antibody according to any of the prior paragraphs, which further comprises an antigen, cell, tissue, or organ.

Also it is an object of the invention to provide a pharmaceutical composition comprising a therapeutically or prophylactically effective amount of at least one humanized anti-human CD154 antibody according to any of the prior paragraphs, which further comprises an autoantigen, allergen, inflammatory agent, drug, or a non-HLA matched (allo) or xeno (non-human) donor cell.

Also it is an object of the invention to provide a method of immunosuppression or immunotherapy using an antibody or composition according to any of the prior paragraphs.

Also it is an object of the invention to provide a method of treating a subject with an allergic, inflammatory, or autoimmune disorder or a transplant recipient by administering an antibody or composition according to any of the prior paragraphs.

Also it is an object of the invention to provide a method of treating or preventing GVHD in a subject by administering an antibody or composition according to any of the prior paragraphs before, concurrent or after transplant of donor tissue, organ, or cells which optionally may be genetically engineered e.g., CAR-T (chimeric antigen receptor T cells) or NK (natural killer) cells.

Also it is an object of the invention to provide a method of eliciting tolerance or prolonged antigen specific immunosuppression by administering an antibody or composition according to any of the prior paragraphs, wherein the method optionally further includes the administration of a cell, antigen, tissue, or organ which comprises an antigen against which tolerance or prolonged immunosuppression is to be elicited.

Also it is an object of the invention to provide a method of gene, cell, tissue or organ therapy which includes administering an antibody or composition according to any of the prior paragraphs.

Also it is an object of the invention to provide a method of treating a condition selected from psoriasis, rheumatoid arthritis, psoriatic arthritis, oophoritis, lupus or SLE, diabetes, IBD, Crohn's disease, ITP, thyroiditis, rheumatoid arthritis, Myasthenia gravis, systemic lupus erythematosus, Graves' disease, idiopathic thrombocytopenia purpura, hemolytic anemia, diabetes mellitus, inflammatory bowel disease, Crohn's disease, multiple sclerosis, psoriasis, drug-induced autoimmune diseases, or drug-induced lupus by administering an antibody or composition according to any of the prior paragraphs.

Also it is an object of the invention to provide a method of treating bone marrow, an organ or immune cells which are for use in cell therapy or an organ or bone marrow transplant comprising incubating said bone marrow, organ, tissue or immune cells with an antibody or composition according to any of the prior paragraphs, e.g., wherein the treated bone marrow, tissue, an organ or immune cells comprise donor and/or recipient T cells.

Also it is an object of the invention to provide a method of inducing tolerance without eliciting thrombotic events in a patient in need thereof comprising administering to a patient an effective amount of an antibody or according to any of the prior paragraphs, which optionally further includes administration of an antigen e.g., an autoantigen, allergen, inflammatory agent, drug, or a non-HLA matched (allo) donor cell.

Also it is an object of the invention to provide a method of inducing tolerance, prolonged immune or T or B cell suppression in a patient who is to receive or has received transplanted cells, organ or tissue, e.g., wherein the drug is a biologic such as a therapeutic antibody, receptor, fusion protein, hormone, growth factor or cytokine.

Also it is an object of the invention to provide a method of treating a T cell mediated autoimmune disorder by administering an effective amount of an antibody or composition according to any of the prior paragraphs.

Also it is an object of the invention to provide a method of treating a B cell mediated autoimmune disorder by administering an effective amount of an antibody or composition according to any of the prior paragraphs.

Also it is an object of the invention to provide a method of treating an autoimmune disease selected from rheumatoid arthritis, Myasthenia gravis, systemic lupus erythematosus, Graves' disease, Huntington's disease, idiopathic thrombocytopenia purpura, hemolytic anemia, diabetes mellitus, Parkinson's disease, psoriasis, Addison's disease, multiple sclerosis, lupus, and drug-induced autoimmune diseases, e.g., drug-induced lupus by administering an effective amount of an antibody or composition according to any of the prior paragraphs.

Also it is an object of the invention to provide a method of treating according to any of the prior paragraphs which includes administration of an antigen.

Also it is an object of the invention to provide a method of treating or preventing GVHD, bone marrow transplant (BMT), multiple sclerosis, lupus, ITP, rheumatoid arthritis, asthma, IBD or another inflammatory bowel disorder by administering an effective amount of an antibody or composition according to any of the prior paragraphs.

Also it is an object of the invention to provide a method for treating a human condition, disorder or disease mediated in whole or in part by CD40 signaling, or a symptom of any of the foregoing, the method comprising administering an effective amount of an antibody or composition according to any of the prior paragraphs, e.g., wherein the human condition, disorder or disease is an inflammatory, allergic, or autoimmune response or fibrosis or the human condition, disorder or disease is selected from lupus nephritis, rheumatoid arthritis, systemic lupus erythematosus, spondyloarthritis, drug-induced lupus erythematosus, inflammatory bowel disease, Crohn's disease, psoriasis and multiple sclerosis or the human condition, disorder or disease is selected from allergic contact dermatitis, alopecia universalis, anaphylactoid purpura asthma, severe asthma, metabolic asthma, allergic asthma, atopic dermatitis, dermatitis herpetiformis, erythema elevatum diutinum, erythema marginatum, erythema multiforme; erythema nodosum, allergic granulomatosis, granuloma annulare, granulocytopenia, hypersensitivity pneumonitis, keratitis, nephrotic syndrome, overlap syndrome, pigeon breeder's disease, idiopathic polyneuritis, urticaria, uveitis, juvenile dermatomyosistitis, and vitiligo or the human condition, disorder or disease is selected from allergic bronchopulmonary aspergillosis; autoimmune hemolytic anemia; acanthosis nigricans; allergic contact dermatitis; Addison's disease; atopic dermatitis; alopecia areata; alopecia universalis; amyloidosis; anaphylactoid purpura; anaphylactoid reaction; aplastic anemia; angioedema, hereditary; angioedema, idiopathic; ankylosing spondylitis; arteritis, cranial; arteritis, giant cell; arteritis, Takayasu's; arteritis, temporal; asthma; ataxia-telangiectasia; autoimmune oophoritis; autoimmune orchitis; autoimmune polyendocrine failure; Behget's disease; Berger's disease; Buerger's disease; bullous pemphigus; candidiasis, chronic mucocutaneous; Caplan's syndrome; post-myocardial infarction syndrome; post-pericardiotomy syndrome; carditis; celiac sprue; Chagas's disease; Chediak-Higashi syndrome; Churg-Strauss disease; Cogan's syndrome; cold agglutinin disease; crest syndrome; Crohn's disease; cryoglobulinemia; cryptogenic fibrosing alveolitis; dermatitis herpetiformis; dermatomyositis; diabetes mellitus; Diamond-Blackfan syndrome; DiGeorge syndrome; discoid lupus erythematosus; eosinophilic fasciitis; episcleritis; erythema elevatum diutinum; erythema marginatum; erythema multiforme; erythema nodosum; familial Mediterranean fever; Felty's syndrome; fibrosis pulmonary; glomerulonephritis, anaphylactoid; glomerulonephritis, autoimmune; glomerulonephritis, post-streptococcal; glomerulonephritis, post-transplantation; glomerulopathy, membranous; Goodpasture's syndrome; graft-vs.-host disease; granulocytopenia, immune-mediated; granuloma annulare; granulomatosis, allergic; granulomatous myositis; grave's disease; Hashimoto's thyroiditis; hemolytic disease of the newborn; hemochromatosis, idiopathic; Henoch-Schönlein purpura; hepatitis, chronic active and chronic progressive; histiocytosis x; hypereosinophilic syndrome; idiopathic thrombocytopenic purpura; job's syndrome; juvenile dermatomyositis; juvenile rheumatoid arthritis (juvenile chronic arthritis);

Kawasaki's disease; keratitis; keratoconjunctivitis sicca; landry-guillain-barre-strohl syndrome; leprosy, lepromatous; Loeffler's syndrome; Lyell's syndrome; lyme disease; lymphomatoid granulomatosis; mastocytosis, systemic; mixed connective tissue disease; mononeuritis multiplex; Muckle-Wells syndrome; mucocutaneous lymph node syndrome; mucocutaneous lymph node syndrome; multicentric reticulohistiocytosis; multiple sclerosis; myasthenia gravis; mycosis fungoides; necrotizing vasculitis, systemic; nephrotic syndrome; overlap syndrome; panniculitis; paroxysmal cold hemoglobinuria; paroxysmal nocturnal hemoglobinuria; pemphigoid; pemphigus; pemphigus erythematosus; pemphigus foliaceus; pemphigus vulgaris; pigeon breeder's disease; pneumonitis, hypersensitivity; polyarteritis nodosa; polymyalgia rheumatica; polymyositis; polyneuritis, idiopathic; Portuguese familial polyneuropathics; pre-eclampsia/eclampsia; primary biliary cirrhosis; progressive systemic sclerosis (scleroderma); psoriasis; psoriatic arthritis; pulmonary alveolar proteinosis; pulmonary fibrosis, Raynaud's phenomenon/syndrome; Reidel's thyroiditis; Reiter's syndrome, relapsing polychondritis; rheumatic fever; rheumatoid arthritis; sarcoidosis; scleritis; sclerosing cholangitis; serum sickness; Sezary syndrome; Sjögren's syndrome; Stevens-Johnson syndrome; Still's disease; subacute sclerosing panencephalitis; sympathetic ophthalmia; systemic lupus erythematosus; transplant rejection; ulcerative colitis; undifferentiated connective tissue disease; urticaria, chronic; urticaria, cold; uveitis; vitiligo; Weber-Christian disease; Wegener's granulomatosis; and Wiskott-Aldrich syndrome.

DETAILED DESCRIPTION

Prior to disclosing the invention in detail the following definitions are provided. Unless defined otherwise, all technical and scientific terms used herein have the same meaning as commonly understood to one of ordinary skill in the art to which this invention belongs.

The term "antibody" as it is used herein with respect to the invention, includes an isolated, recombinant or synthetic antibody, antibody conjugate or antibody derivative. The term "antibody" is often intended to include an antibody fragment, including an antigen-binding fragment, unless otherwise indicated or understood by context. An antigen-binding fragment competes with the intact antibody for specific binding. See generally, Fundamental Immunology, Ch. 7 (Paul, W., ed., 2nd ed. Raven Press, N.Y. (1989)). Antigen-binding fragments may be produced by recombinant DNA techniques or by enzymatic or chemical cleavage of intact antibodies. In some embodiments, antigen-binding fragments include Fab, F(ab)$_2$, Fab', F(ab')$_2$, F(ab')$_3$, Fd, Fv, domain antibodies (dAb), other monovalent and divalent fragments, complementarity determining region (CDR) fragments, single-chain antibodies (e.g., scFv, scFab, and scFabδC), chimeric antibodies, diabodies, triabodies, minibodies, nanobodies, and polypeptides that contain at least a portion of an antibody that is sufficient to confer specific antigen binding to the polypeptide; and fusions and derivatives of the foregoing. See, e.g., Holliger and Hudson, Nature Biotechnology 23: 1126-1136 (2005) and Hust et al., BMC Biotech 7: 14 (2007).

Unless otherwise stated or where otherwise implied by context, an "antibody" of the present invention includes whole antibodies and any antigen-binding fragments thereof, antibody derivatives or variants that may contain one or more modifications (e.g., an amino acid insertion, deletion, substitution, a post-translational modification or lack thereof, etc.), including antibody conjugates (i.e., antibody or antigen-binding fragment thereof conjugated to or associated with a functional moiety). The antibody derivatives, including antibody conjugates, may be based on or may comprise an antigen-binding fragment of the invention that specifically binds CD154. Additionally, the aforementioned antibody embodiments may be murine, hamster, goat, rabbit, chimeric, humanized, or fully human antibodies, fragments, derivatives, or conjugates. It is understood that in certain aspects of the invention, the term "antibody" may exclude one or more of the antibody embodiments recited above; such conditions will be evident to the skilled artisan.

The term "effector function" refers to the functional ability of the Fc or constant region of an antibody to bind proteins and/or cells of the immune system. Antibodies having reduced effector function and methods for engineering such antibodies are well-known in the art (see, e.g., WO 05/18572, WO 05/03175, and U.S. Pat. No. 6,242,195) and are described in further detail herein. Typical effector functions include the ability to bind complement protein (e.g., the complement protein C1q), and/or an Fc receptor (FcR) (e.g., FcγRI, FcγRII, FcγRIIa, FcγRIII, and/or FcγRIIIb). The functional consequences of being able to bind one or more of the foregoing molecules include, without limitation, opsonization, phagocytosis, antigen-dependent cellular cytotoxicity (ADCC), complement-dependent cytotoxicity (CDC) and/or effector cell modulation. A decrease in effector function refers to a decrease in one or more of the biochemical or cellular activities induced at least in part by binding of Fc to its cognate receptor or to a complement protein or effector cell, while maintaining the antigen-binding activity of the variable region of the antibody (or fragment thereof), albeit with reduced, similar, identical, or increased binding affinity. Particular antibodies of the invention exhibit reduced effector function. Decreases in effector function, e.g., Fc binding to an Fc receptor or complement protein, can be expressed in terms of fold reduction (e.g., reduced by 1.5-fold, 2-fold, and the like) and may be calculated based on, e.g., the percent reductions in binding activity determined using binding assays known in the art (see, for example, WO 05/18572).

Unless otherwise required by context, singular terms shall include pluralities and plural terms shall include the singular.

Throughout this specification and claims, the word "comprise," or variations such as "comprises" or "comprising" will be understood to imply the inclusion of a stated integer or group of integers but not the exclusion of any other integer or group of integers.

The term "CD154" refers to a ligand expressed on activated T cells. CD154 is known by several other names in the art, such as CD40 ligand (CD40L), CD40 counter receptor (CD40CR), gp39, T-BAM, T-Cell Activating Molecule, TRAF, TNF-Related Activation Protein (TRAP), and Tumor Necrosis Factor Ligand Superfamily Member 5 (TNFSF5) (Gauchat et al., 1993 *FEBS Lett.* 315: 259-266; Graf et al. 1992, *Europ. J. Immun.* 22: 3191-3194; Hollenbaugh et al., 1992 *EMBO J.* 11: 4313-4321). These terms are used interchangeably throughout this application. The CD154 binding proteins, including antibodies, of this invention specifically bind to human CD154 and may cross react and therefore specifically bind to CD154 of other species. In certain embodiments, the CD154 binding proteins, including antibodies, of this invention specifically bind to human CD154, mouse CD154 or non-human primate CD154.

The term "anti-CD154 antibody" also encompasses a synthetic antibody or a recombinant antibody that is generated using recombinant DNA technology, such as, for example, an antibody expressed by a bacteriophage. The term "anti-CD154 antibody" should also be construed to include an antibody that has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology that is available and well known in the art.

"Mutation or mutations that eliminate or reduces FcR binding and which eliminates toxicity" herein refers to a mutation or mutations that eliminate or reduce thrombocytopenia or thrombosis or clotting in vitro and/or in vivo. Sites in the Fc or constant regions of different human antibody types including human IgG1, IgG2, IgG3 and IgG4 which may be modified to eliminate or reduce FcR binding and affect (impair or enhance) other Fc effector functions are well known in the art. Exemplary mutations which may be modified in the human IgG1 Fc or constant region are identified in Tables 1-3 and in the examples infra.

"Mutation or mutations that eliminate or reduce complement function and which maintain tolerance inducing properties" refers to mutation or mutations in human, chimeric, or humanized antibodies containing human constant regions, preferably human IgG1 or IgG3 constant regions, wherein the Fc region thereof has been mutated at one or more sites in order to eliminate or substantially reduce complement binding. Preferably such mutations will not appreciably affect the ability of the antibody to induce tolerance in vivo. This may be established using appropriate tolerance models such as the skin transplant model. Sites in the Fc or constant regions of different human antibody types including human IgG1, IgG2, IgG3 and IgG4 which may be modified to eliminate or reduce complement binding and which may affect (impair or enhance) other Fc effector functions are well known in the art. Exemplary sites which may be modified in IgG1 are identified in Tables 1-3 and the examples infra.

A "patient" can mean either a human or non-human animal, preferably a mammal. In preferred embodiments this invention produces anti-human CD154 antibodies suitable for human therapy containing mutated IgG1 or IgG3 constant regions, wherein such mutations eliminate or substantially inhibit toxicity or safety concerns such as thrombocytopenia or thrombosis or clotting reactions or toxicity associated with complement reactions and preferably wherein such antibodies retain the ability to induce tolerance or prolonged humoral suppression in vivo.

As used herein, "subject", as refers to an organism or to a cell sample, tissue sample or organ sample derived therefrom, including, for example, cultured cell lines, biopsy, blood sample, or fluid sample containing a cell. In many instances, the subject or sample derived therefrom comprises a plurality of cell types. In one embodiment, the sample includes, for example, a mixture of tumor and normal cells. In one embodiment, the sample comprises at least 10%, 15%, 20%, et seq., 90%, or 95% tumor cells. The organism may be an animal, including but not limited to, an animal, such as a cow, a pig, a mouse, a rat, a chicken, a cat, a dog, etc., and is usually a mammal, such as a human.

The term "treating" in its various grammatical forms in relation to the present invention refers to preventing (i.e. chemoprevention), curing, reversing, attenuating, alleviating, minimizing, suppressing, or halting the deleterious effects of a disease state, disease progression, disease causative agent (e.g. bacteria or viruses), or other abnormal condition. For example, treatment may involve alleviating a symptom (i.e., not necessarily all the symptoms) of a disease of attenuating the progression of a disease.

"Treatment or prevention of autoimmunity" or "treating or preventing" another disease condition such as cancer, infection, inflammation, allergy, transplant, graft versus host disease and other conditions wherein anti-CD154 antibodies are potentially of therapeutic benefit as used herein, refers to partially or totally inhibiting, delaying, or preventing the progression of the disease. In the case of cancer this means treating or inhibiting cancer metastasis; inhibiting, delaying, or preventing the recurrence of cancer including cancer metastasis; or preventing the onset or development of cancer (chemoprevention) in a mammal, for example, a human. In addition, the methods of the present invention may be practiced for the treatment of human patients with cancer. However, it is also likely that the methods would also be effective in the treatment of cancer in other mammals. In the preferred embodiments the subject antibodies are used to treat autoimmunity, allergy, inflammation, transplant, GVHD, bone marrow transplant (BMT), and to induce antigen specific tolerance or prolonged antigen-specific immunosuppression, particularly suppression of T cell and/ or B cell differentiation, activation and/or proliferation in subjects in need thereof. Preferred indications include mul- tiple sclerosis, lupus or SLE, ITP, IBD, Crohn's disease, inflammatory bowel disease, Crohn's disease, psoriasis, uveitis, rheumatoid arthritis, asthma, GVHD, bone marrow transplant, diabetes, rheumatoid arthritis, psoriatic arthritis, psoriasis, cell transplant, tissue transplant, organ transplant, bone marrow transplant, cell and gene therapy, oophoritis and thyroiditis.

As used herein, the term "therapeutically effective amount" is intended to qualify the amount of the treatment in a therapeutic regiment necessary to treat a condition e.g., autoimmunity, allergy, inflammation, GVHD or transplant or to decrease or eliminate an immune response, especially a T cell or B cell antibody response against an antigen such as an autoantigen, allergen, inflammation inducing agent, transplanted cell, tissue, or organ or against a drug such as a biologic, e.g., a therapeutic antibody, Ig fusion protein, hormone, growth factor, or other therapeutic protein or polypeptide.

As used herein, the term "prophylactically effective amount" is intended to qualify the amount of the treatment in a therapeutic regiment necessary to prevent a condition, or the progression and symptoms of a disease e.g., autoim- munity, allergy, inflammation, GVHD or anti-transplant, drug or rejection response.

The present invention provides an improved anti-CD154 antibody for use in human therapy which was derived from a humanized antibody IDEC-131 developed by IDEC Phar- maceuticals (now BiogenIDEC). IDEC-131 is a high affinity antibody which as detected by BIAcore at 25° C. binds to human CD154 with a $K_D$ of 151 pm.

IDEC131 is a humanized anti-CD154 antibody of the human IgG1 isotype that was derived from a mouse anti- human CD154 antibody (24-31), which is disclosed in U.S. Pat. No. 5,747,037. A hybridoma cell line secreting the 24-31 which is commercially available was deposited at the American Type Tissue Collection and the deposited cell line designated by ATCC Accession No. HB1712.

The sequence of IDEC-131, and the use thereof in treating various allergic, autoimmune and inflammatory indications and for suppressing T and B cell mediated immune responses is disclosed in U.S. Pat. Nos. 6,001,358; 6,440, 418; 6,506,383; 7,074,406 and 7,122,187. Based on its properties including its potent immunosuppressive effects on T and B cell immunity and high affinity IDEC-131 was advanced into human clinical trials. Particularly, IDEC-131 has been used in human clinical trials sponsored by IDEC for treating 2 autoimmune indications, i.e., Idiopathic Thrombocytopenia Purpura ("ITP") and remitting/relapsing multiple sclerosis ("RR-MS"). While these clinical trials with IDEC-131 showed some clinical efficacy trials (even though very early on, relatively few patients), they were halted after it was reported that another IgG1 anti-human CD154 antibody developed by Biogen, also derived from a murine anti-human CD154 antibody, (murine 5c8 antibody isolated by Seth Lederman of Columbia University) elicited adverse effects in human patients. Particularly, when the Biogen chimerized 5c8 antibody was used in clinical trials it resulted in adverse thrombogenic events ("TE's") which resulted in stroke and death in several patients in the clinical trial. The present invention addresses these problems as obtaining other advantages pharmacokinetic vis-à-vis IDEC-131.

By contrast, the invention provides a humanized variant anti-human CD154 antibody derived from IDEC-131, which like IDEC-131 is of the human IgG1 isotype however, its Fc region has been engineered to eliminate both FcR binding and complement activation. Particularly, its constant region is engineered to contain E269R and K322A mutations (wherein these mutated residues are numbered according to the Kabat antibody numbering system). These mutations respectively result in reduced FcγRIIa and to C1q binding. Particularly the resultant modified antibody has restricted FcR/C1q binding, i.e., it does not bind to FcRγ2 or to FcRγ3 on platelets and does not bind or activate complement. By contrast its binding to FcRn is unaffected. As disclosed infra, and supported by experimental data disclosed herein anti- CD154 IgG1 antibodies containing these mutations when assayed in different experimental models do not exhibit any detectable pro-thrombotic activities in vitro or in vivo on murine or human platelets.

Also, the variable heavy and light sequences of IDEC-131 were further engineered by affinity maturation. Affinity maturation was conducted with the hope of enhancing the binding affinity of the resultant anti-human CD154 antibody compared to IDEC-131 while still maintaining its desired immunosuppressive properties. However, this result was far from assured since as mentioned IDEC-131 already has strong binding affinity for human CD154 (161 pm) and is potently immunosuppressive in different models (EAE, humoral immune suppression and allospecific tolerance models).

After much experimentation and successive screening methods mutated versions of the variable heavy and light chains of IDEC-131 were obtained that yielded humanized antibodies (including INX021) having improved affinity relative to IDEC-131. Specifically INX021 was obtained as well as 12 other variants. These humanized variants were assessed and INX021 was selected as the lead candidate for human therapy based on its beneficial binding (≅5-fold greater affinity to human CD154 than IDEC-131) and also it possesses better functional (immunosuppressive) properties compared to IDEC-131 and also compared to other variants.

As shown in FIGS. 1A-C (which contains the sequences of the inventive humanized IgG1 anti-human CD154 anti- body, INX021), this antibody contains two mutations in the heavy chain CDR3, three mutations in the light chain CDR1 and two mutations in the light chain CDR3 (compared to IDEC-131). Therefore, a total of 7 CDR residues were modified. Unexpectedly as shown infra, the resultant humanized anti-human CD154 antibody binds to human CD154 with about 5-fold greater affinity than the parent antibody which as noted previously itself binds to human CD154 with very high affinity. This is surprising as even a single CDR modification may have drastic effects on antibody binding affinity. Also, it is not predictable that the affinity of antibodies already of relatively high affinity may be improved.

This modified humanized antibody when assayed in different in vitro and in vivo models possesses very potent immunosuppressive properties. Specifically, INX021 potently suppresses humoral immunity, EAE and it induces allospecific tolerance or prolonged antigen-specific T cell non-responsiveness. As shown infra, INX021 elicits more potent inhibition of T cell CD154-driven B cell activation relative to IDEC-131.

Therefore, the inventive antibody (compared to IDEC-131):

(i) possesses a 5-fold greater binding affinity for human CD154 than IDEC-131, (ii) it more potently elicits immunosuppressive activities compared to IDEC-131, (iii) like IDEC-131 it suppresses T and B (humoral) immunity, for example it suppresses EAE and it induce allospecific tolerance, and (iv) it exhibits an improved safety profile compared to IDEC-131 because of mutations in the Fc region which substantially reduce FcR and C1q binding and as a consequence it does not exhibit any detectable pro-thrombotic activities in vitro or in vivo on murine or human platelets.

Based on these combined properties the subject anti-human CD154 antibody is well suited for use in human therapy as it should exhibit an enhanced safety profile in patients and should be more potent and therefore more efficacious than IDEC-131. It is anticipated that the enhanced binding affinity of this antibody should facilitate its administration via subcutaneous dosing. This is beneficial for its potential use in treating chronic human indications.

Also, the subject antibody because it is an intact, i.e., it comprises a full length IgG1 may afford pharmacokinetic and safety advantages to the Pegylated Fab being developed by Biogen/UCB and to the CD154 specific diabody being developed by Bristol Meyers Squibb.

Additionally, because the subject antibody possesses a higher potency this may further enhance dosing as potentially the antibody may be administered less frequently. This is important as most applications of the subject antibody are for the treatment of chronic human autoimmune, allergic or inflammatory indications wherein repeated dosing will be required for any effective therapeutic regimen. Particularly, the inventive antibody should be well suited for treatments wherein B or T cell immunosuppression is therapeutically desired.

Therefore, in this application the Applicant provides novel and improved humanized anti-human CD154 antibodies for use in human immunotherapy having improved affinity and other pharmacokinetic properties, which should not elicit toxicity in human patients, particularly these antibodies should not elicit platelet aggregation or thromboembolic events in human subjects, and moreover, based on their further inability to bind and activate complement they further should not mediate ADCC or CDC mediated cytotoxicity. As shown in the examples the inventive antibody possesses substantially improved functional and pharmacokinetic properties vis-à-vis IDEC131 and to another CD154 antibody previously used in human therapy. Therefore, this antibody which should afford clinical benefits when used in human therapy.

While the inventive antibody INX021 contains 2 mutations which respectively reduce FcRγ2 and 3 binding, and C1q binding, it is further envisioned that other mutations in the Fc region may be introduced which may further reduce binding to other Fc receptors or complement or alter other effector functions. Examples of other possible mutations are known in the art e.g., Shields R L, Namenuk A K, Hong K, et al., ("High resolution mapping of the binding site on Human IgG1 for Fc for FcγRI, Fc for FcγRII, Fc for FcγRIII, and FcRn") reports the design of IgG1 variants with impaired binding to the Fc for FcγR. J Biol. Chem. 2001; 276: 6591-604) In addition, US20070237767 and US20100104564) describe Fc mutagenesis to eliminate FcR binding. Also, specific Fc mutations and the effects thereof are listed in the Table 1-3 below. These mutations are intended to be exemplary and not exhaustive of other mutations and combinations thereof known to promote or impair Fc effector functions such as FcR binding, complement binding, glycosylation, ADCC activity, CDC activity, FcRN binding, among others.

TABLE 1

(from Shields et al., "High resolution mapping of the binding site on Human IgG1 for Fc for FcγRI, Fc for FcγRII, Fc for FcγRIII, and FcRn", J Biol Chem 2001; 276: 6591-604)

| Fc mutation | FcγRI | FcγRIIa | FcγRIIb | FcγRIIIa | FcRn |
|---|---|---|---|---|---|
| E233P | 0.12 | 0.08 | 0.12 | 0.04 | 0.54 |
| D265A | 0.16 | 0.07 | 0.13 | 0.09 | 1.23 |
| D265N | | 0.02 | 0.03 | 0.02 | |
| D270N | | 0.03 | 0.05 | 0.04 | |
| N297A | 0.15 | 0.05 | 0.1 | 0.03 | 0.8 |
| S298N | | 0.05 | 0.08 | 0.06 | |
| P329A | 0.48 | 0.08 | 0.12 | 0.21 | 0.8 |
| D270A | 0.76 | 0.06 | 0.1 | 0.14 | 1.05 |

TABLE 2

(from US20100104564)

| Fc mutation | FcγRI | FcγRIIa (H131) | FcγRIIa (R131) | FcγRIIb | FcγRIIIa (V158) | FcγIIIa (F158) |
|---|---|---|---|---|---|---|
| K326V | 0.52 | 0.01 | 0.01 | 0.02 | 0.87 | 2.34 |
| V369R | 0.79 | 0.01 | 0.02 | 0.03 | 0.93 | 1.64 |
| F405K | 1.52 | 0.02 | 0.02 | 0.02 | 1.08 | 2.55 |
| L410P | 1.27 | 0.01 | 0.01 | 0.01 | 0.99 | 1.75 |
| V427R | 1.69 | 0.03 | 0.05 | 0.03 | 1.27 | 0.59 |

TABLE 3

(from US20070237767)

| Variant # | Fc mutation | FcγRI | FcγRIIa | FcγRIIb | FcγRIIc | FcγRIIIa | C1q | FcRn |
|---|---|---|---|---|---|---|---|---|
| 113 | L234N | 0.1 | 0.19 | 2.05 | | 0.49 | 1.18 | 1.06 |
| 744 | G237M | 0.07 | 0.14 | 0.57 | 0.66 | 0.1 | 1.8 | 1.74 |

TABLE 3-continued (from US20070237767)

| Variant # | Fc mutation | FcγRI | FcγRIIa | FcγRIIb | FcγRIIc | FcγRIIIa | C1q | FcRn |
|---|---|---|---|---|---|---|---|---|
| 88 | S239F | 0.28 | 0.02 | 0.33 | | 0.1 | 0.95 | 0.85 |
| 826 | V262E | 1.03 | 0.16 | 0.92 | 36.47 | | 2.85 | 9.27 |
| 76 | V264F | 0.43 | 0.05 | 0.22 | | 0.06 | 1.87 | 1.07 |
| 143 | V266T | 0.28 | 0.1 | 0.16 | 0.18 | | 1.21 | 0.53 |
| 228 | S267N | 0.72 | 0.08 | | | 0.27 | 3.18 | 0.85 |
| 148 | E269R | 0.07 | 0.07 | 0.13 | 0.06 | 0.05 | 1.15 | 0.72 |
| 779 | N286E | | 0.07 | 0.38 | 0.37 | 0.01 | 0 | 2.12 |
| 858 | N297R | 0.01 | 0.01 | 0.01 | 0.06 | 0.01 | | 0.45 |
| 80 | T299A | 0.01 | 0.1 | 0.56 | 72.84 | 0.06 | 2.31 | 0.82 |
| 870 | R301D | 0.87 | 0.11 | 0.06 | 0.04 | 0.03 | 1.58 | 0.5 |
| 84 | N325L | 0.42 | 0.04 | 1.46 | | 0.03 | 2.18 | 0.91 |
| 161 | N325E | 1.34 | 0.09 | 0.05 | 0.03 | <0.02 | 0.86 | 0.55 |
| 473 | L328R | 0.07 | 0.1 | 0.88 | 0.37 | 0.11 | 1.21 | 1.82 |

Based on this combination of safety, functional and pharmacokinetic properties the inventive humanized anti-human CD154 IgG1 antibodies may be used to treat or prevent conditions wherein suppression of T and/or B cell activation, differentiation and proliferation is therapeutically desired such as allergic, autoimmune, transplant (allo or xenogeneic organ, cell, tissue transplants) and inflammatory conditions. Particular non-limiting examples thereof include by way of example multiple sclerosis, systemic lupus erythematosus (SLE), other forms of lupus, autoimmune thrombocytopenia (ITP), kidney transplant, skin and islet transplant, rheumatoid arthritis, sarcoidosis, psoriatic arthritis, Crohn's disease, inflammatory bowel disease, Crohn's disease, COPD, asthma, diabetes, thyroiditis, graft versus host disease, bone marrow (BM) or hematopoietic stem cell transplantation, and atherosclerosis. As well some of these variants including INX021 possess increased potency efficacy, including the ability to elicit tolerance in vivo.

As evidenced by experimental data a particularly contemplated application of the inventive antibodies including INX021 is for alleviating or preventing anti-drug reactions, particularly those elicited against biologics and other drugs such as therapeutic antibodies, fusion proteins, hormones, growth factors, enzymes, peptides, antibiotics, antivirals, and the like. This may enable these drugs to be administered for more prolonged duration, may increase the number of patients who respond to the drug, and/or may facilitate the efficacy of the drug intreated patients.

As discussed herein, other sites in the Fc region of human IgG1 and other human constant regions are known to be involved in complement binding and/or activation as well as FcR binding. Accordingly, the described mutations are exemplary of appropriate mutations in the Fc region of IgG1 or IgG3 or other antibodies that result in loss of one or both of complement binding and FcR binding.

The tolerance inducing or prolonged (T or B) immunosuppressive effects of the complement-binding mutant αCD154 variants or variants thereof may be evaluated in a well-studied model of haplo-mismatched skin allograft survival, where long-term tolerance is induced by the administration of αCD154 and alloantigen. However, other tolerance models may alternatively be used to assess the ability of a αCD154 complement deficient and/or FcR deficient variants (containing a mutated Fc region) to induce tolerance.

The thromboembolic activities of the FcR mutated αCD154 may be tested in a murine model expressing the human FcγRIIA receptor that reproduces the events observed in NHP (Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., "The contribution of Fc effector mechanisms in the efficacy of anti-CD154 immunotherapy depends on the nature of the immune challenge". Int Immunol 2004. 16: 1583-1594). In such mice, treatment with αCD154 (anti-mouse CD154) induces pulmonary thrombi; therefore the loss of FcR binding in anti-CD154 antibodies containing mutated human Fc regions (mutated IgG1 constant regions) eliminates or appreciably reduces the formation of thrombi. Using this or comparable models the effects of specific Fc mutations on the toxicity associated with αCD154 therapy may be determined.

Again, the mutated CD154 specific antibodies of the present invention which are derived from IDEC-131, may be used for the treatment and prevention of any condition wherein antagonizing the effects of CD154 including CD154/CD40 signaling, or blocking or inhibiting CD154 binding to CD40 may be therapeutically effective, and may reduce the symptoms of the disease. Examples thereof include the treatment of allergic, autoimmune, cancer, transplant, GVHD, inflammatory and other conditions, especially conditions wherein the induction of tolerance and/or the suppression of humoral immunity or T cell immunity are therapeutically desirable. Specific examples include multiple sclerosis, rheumatoid arthritis, inflammatory bowel disease, Crohn's disease, thyroiditis, lupus erythematosus, autoimmune thrombocytopenia, diabetes, graft versus host disease, cell therapy, organ and tissue transplant, e.g., kin, kidney, pancreas, bone marrow, atherosclerosis, and other conditions where humoral or T cell suppression is desired.

The subject antibodies which target CD154 possess improved safety properties are of great therapeutic potential as CD154 is an extremely attractive target for immune intervention in a wide spectrum of autoimmune, and graft-related diseases. Virtually all models of autoimmune disease in mice tested to date are therapeutically ameliorated by αCD154 treatment. Beyond simply blocking CD154-CD40 interactions, αCD154 therapy leads to the induction of immunologic tolerance (Prevention of transplant rejection by blocking CD40-CD154 interactions has been repeatedly documented for the induction of long-term tolerance to skin, Gordon, E. J., Markees, T. G., Phillips, N. E., Noelle, R. J., Shultz, L. D., Mordes, J. P., Rossini, A. A. and Greiner, D. L., "Prolonged survival of rat islet and skin xenografts in mice treated with donor splenocytes and anti-CD154 monoclonal antibody", Diabetes 1998. 47: 1199-1206; Markees, T. G., Phillips, N. E., Noelle, R. J., Shultz, L. D., Mordes, J. P., Greiner, D. L. and Rossini, A. A., "Prolonged survival of mouse skin allografts in recipients treated with donor splenocytes and antibody to CD40 ligand", *Transplantation* 1997. 64: 329-335; Jarvinen, L. Z., Blazar, B. R., Adeyi, O. A., Strom, T. B. and Noelle, R. J., "CD154 on the surface of CD4+CD25+ regulatory T cells contributes to skin transplant tolerance", *Transplantation* 2003. 76: 1375-1379; Quezada, S. A., Fuller, B., Jarvinen, L. Z., Gonzalez, M., Blazar, B. R., Rudensky, A. Y., Strom, T. B. and Noelle, R. J., "Mechanisms of donor-specific transfusion tolerance: preemptive induction of clonal T-cell exhaustion via indirect presentation", *Blood* 2003. 102: 1920-1926; Frleta, D., Lin, J. T., Quezada, S. A., Wade, T. K., Barth, R. J., Noelle, R. J. and Wade, W. F., "Distinctive maturation of in vitro versus in vivo anti-CD40 mAb-matured dendritic cells in mice", *J Immunother* 2003. 26: 72-84; Quezada, S., Eckert, M., Schned, A., Noelle, R. J. and Burns, C., "Distinct mechanisms of action of anti-CD154 in early versus late treatment of murine lupus nephritis", *Arth Rheum.* 2003; Elster, E. A., Xu, H., Tadaki, D. K., Montgomery, S., Burkly, L. C., Berning, J. D., Baumgartner, R. E., Cruzata, F., Marx, R., Harlan, D. M. and Kirk, A. D., "Treatment with the humanized CD154-specific monoclonal antibody, hu5C8, prevents acute rejection of primary skin allografts in nonhuman primates, Transplantation", 2001. 72: 1473-1478, islets (Benda, B., Ljunggren, H. G., Peach, R., Sandberg, J. O. and Korsgren, O., "Co-stimulatory molecules in islet xenotransplantation: CTLA4Ig treatment in CD40 ligand-deficient mice", *Cell Transplantation* 2002. 11: 715-720) bone marrow (Wekerle, T. and Sykes, M., "Mixed chimerism and transplantation tolerance", *Annual Review of Medicine* 2001, 52: 353-37019, and a myriad of other transplanted organs (Camirand, G., Caron, N. J., Turgeon, N. A., Rossini, A. A. and Tremblay, J. P., "Treatment with anti-CD154 antibody and donor-specific transfusion prevents acute rejection of myoblast transplantation", *Transplantation* 2002. 73: 453-461; Tung, T. H., Mackinnon, S. E. and Mohanakumar, T., "Long-term limb allograft survival using anti-CD154 antibody in a murine model", *Transplantation* 2003. 75: 644-650). Furthermore, αhuman CD154 in NHP has been shown to induce long-term tolerance to allogeneic skin transplants.

General Description of Inventive Methods for Producing Inventive Antibodies

Exemplary Method for Synthesis of Inventive Antibodies

DNA encoding $V_H$ and $V_L$ of hamster αmurine CD154 or IDEC-131 or a variant as disclosed herein were cloned and fused to DNA encoding the human γ 1 CH1, CH2, CH3 region or to the IgG1 variants disclosed herein. The nucleotide sequences were verified using Megabace™ sequence analyzer. A plasmid expression vector, pEE12 containing both heavy and light chains of each of the MR1 variants is transfected into NSO cells and products purified by Protein A chromatography.

Binding of Inventive Antibodies to CD154

Comparison of the binding activity of CD154 antibody variants was determined by their binding to CHO cells transfected with mouse CD154. CD154-expressing CHO cells will be incubated with biotin-labeled αCD154 in the presence of unlabeled αCD154 heavy chain variants or isotype-matched antibodies for 1 hr at 4° C. Binding of biotinylated MR1 will be detected using a streptavidin conjugated fluorochrome and flow cytometry will be performed. The percent of inhibition by variants may be determined by recording reductions in the mean fluorescence intensity of MR1 stained cells.

Antibody Half-Life Using ELISA

ELISA or Biacore may be used to determine the in vivo half-life of αhuman IgG1 variants. Serum concentrations of hIgG1 may be determined at a set time, e.g., 1 month post-administration.

Binding of Variants to FcRs.

Binding of variant IgG1 mAbs to FcR's may be determined by a solid phase assay. Briefly, Maxisorb ELISA plates may be coated with mouse or human FcγRI, FcγRIIA, FcγRIIB, or FcγRIIIA (R & D Systems). Biotinylated versions of the variants may be produced. Binding may be determined by colorimetric detection using enzyme-coupled avidin. Reduction in binding is determined for a variant compared to the WT molecule.

Binding of αCD154 nAbs to Human C1q

This may be effected using known methods or as described herein. Purified human C1 q may be titrated into wells in which the IgG1 variants of MR1 or IDEC-131 have been absorbed onto Maxisorb ELISA plates. Bound C1q will be detected with HRP-chicken anti-C1q. All variants will be compared to the binding of C1q to the WT IgG1 MR1, as described (Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., "The contribution of Fc effector mechanisms in the efficacy of anti-CD154 immunotherapy depends on the nature of the immune challenge", *Int Immunol* 2004. 16: 1583-1594; and Taylor, P. A., Lees, C. J., Wilson, J. M., Ehrhardt, M. J., Campbell, M. T., Noelle, R. J. and Blazar, B. R., "Combined effects of calcineurin inhibitors or sirolimus with anti-CD40L mAb on alloengraftment under nonmyeloablative conditions", Blood 2002. 100: 3400-3407).

Induction of Tolerance with Mutant αCD154 mAbs.

The ability of an anti-CD154 antibody to elicit tolerance or prolonged immunosuppression may be determined by known methods and specifically as described herein. The hamster anti-murine CD154 that was produced in our laboratory MR1 routinely induces long-lived graft tolerance, as we have shown (Quezada, S. A., Fuller, B., Jarvinen, L. Z., Gonzalez, M., Blazar, B. R., Rudensky, A. Y., Strom, T. B. and Noelle, R. J., "Mechanisms of donor-specific transfusion tolerance: preemptive induction of clonal T-cell exhaustion via indirect presentation", *Blood* 2003. 102: 1920-1926; Quezada, S. A., Bennett, K., Blazar, B. R., Rudensky, A. Y., Sakaguchi, S. and Noelle, R. J., "Analysis of the underlying cellular mechanisms of anti-CD154-induced graft tolerance: the interplay of clonal anergy and immune regulation", *J Immunol* 2005. 175: 771-779; Rossini, A. A., Parker, D. C., Phillips, N. E., Dude, F. H., Noelle, R. J., Mordes, J. P. and Greiner, D. L., "Induction of immunological tolerance to islet allografts", *Cell Transplant* 1996. 5: 49-52).

Tolerance is induced by the co-administration of alloantigen (in the form of donor spleen cells) and αCD154. It has been shown that a humanized IgG1 form of MR1 also induces graft tolerance 24, and therefore the WT γ1 variant will serve as a positive control for tolerance induction. The mutant versions of MR1 which have lost the ability to bind complement will be tested for their ability to induce graft tolerance.

Skin grafting is performed as a modification of a technique used by Markees et al. (12). Briefly, age-matched male CB6F1 mice will be used as donors for both spleen cells (DST) and skin grafts. Recipient C57BL/6 mice will injected with or without 5×107 DST cells in 500 μL Hanks balanced salt solution by tail vein injection (intravenously) and 500 μg of WT or mutant αCD154 or control immunoglobulin, hamster or human, (HIgG1) in phosphate-buffered saline (PBS) intraperitoneally on days −3, −5 and −7. Mice will treated with the appropriate antibody (250 μg/injection) 3 times per week, thereafter for the duration of the experiment. On day 0, recipient mice will be anesthetized with 50 μg per gram body weight of each of ketamine and xylazine injected intraperitoneally (15 mg/mL in PBS), and CB6F1 skin grafts will be prepared using established methods. Rejection will be defined as the day on which less than 20% of the skin graft remains. Animals will be evaluated for skin graft rejection for 100 days. In addition, for each of the tolerant groups, skin grafts will be taken at day 100 and evaluated by histochemistry for leukocyte infiltrates and scored based on the number of cells/area measured. Finally, third party transplants (H-2Kskin) will be transplanted on tolerized mice (in selected groups) to assure that the tolerance induced is antigen specific, as has been published previously in this system (Markees, T. G., Phillips, N. E., Noelle, R. J., Shultz, L. D., Mordes, J. P., Greiner, D. L. and Rossini, A. A., "Prolonged survival of mouse skin allografts in recipients treated with donor splenocytes and antibody to CD40 ligand", Transplantation 1997. 64: 329-335, Markees, T., Phillips, N., Gordon, E., Noelle, R. J., Mordes, J. P., Greiner, D. L. and Rossini, A. A., "Improved skin allograft tolerance induced by treatment with donor splenocytes and an extended course of anti-CD154 monoclonal antibody", Transplant Proc 1998. 30: 2444-2446; Markees, T. G., Appel, M. C., Noelle, R. J., Mordes, J. P., Greiner, D. L. and Rossini, A. A., "Tolerance to islet xenografts induced by dual manipulation of antigen presentation and co-stimulation", Transplantation Proceedings 1996. 28: 814-815) of humoral immunity with mutant αCD154 mAbs.

In addition to measuring the impact of the complement and FcR mutations on tolerance, the impact of antibody treatment on the development of primary and secondary humoral immune responses will also be assayed as previously described. Briefly, mice (4/group) will be immunized with chicken ovalbumin in CFA (200 μg/mouse) and treated with the MR1 variants (200μ/mouse×3 times/week). On days 7, 14 and 21, IgM and IgG anti-OVA will be measured by a standardized anti-OVA ELISA and serum concentrations of anti-OVA will be quantified.

Toxicity Studies with Inventive αCD154 mAbs.

The thrombogenic activity of αCD154 has been demonstrated in a murine model using mice that express human FcγRIIA. This model parallels toxicity findings in NHP using both intact and aglycosylated forms of anti-human CD154. Briefly, mice will be injected with preformed immune complexes (IC) of sCD154 (R & D Systems) and each variant of αCD154 (138 μg mAb and 50 g Ag, approximating 500 nM IC at a 1:3 (mAb/Ag) stoichiometric ratio). Following injection, if the mixture is thrombolytic, mice will exhibit prolonged disorientation, shallow breathing, and impaired mobility. Those exhibiting this activity are expected to have marked reductions in platelet counts. After 60 minutes, lungs will be harvested, fixed in formalin, sectioned and H&E-stained. Mouse lung sections will be evaluated for evidence of thrombosis (as measured by intravascular thrombi) and the number of thrombi/section will be counted. For each mouse, 10 sections will be counted and the total number of thrombi compared across all groups treated with the various variants of IgG1 MR1. In addition, total platelet counts (harvested by cardiac puncture at the time of euthanasia), will be evaluated by flow cytometry, and are expected to drop by 80% using those antibodies that are thrombogenic. These findings will determine which of the MR1 variants (FcR binding (N325L, K326V, E269R) are thrombogenic and if alteration of the FcR binding alters this activity.

Blocking the Development of a T Cell Mediated Autoimmune Disease, Experimental Autoimmune Encephalomyelitis (EAE).

Female C57BL/6 mice 5-8 weeks old will be immunized subcutaneously with 200 μg of MOG35-55 peptide emulsified in CFA supplemented with 5 mg/ml of Mycobacterium tuberculosis. The mice will receive intraperitoneal injections with 250 ng pertussis toxin at the time of immunization and 48 hours later. After 7 days, the mice will receive an identical booster immunization with MOG/CFA without pertussis toxin. Clinical disease usually commences between day 16 and day 20 after immunization. Mice will be administered each of the MR1 variants, human IgG (as control for the variants), hamster Tg (as control for MR1) or hamster MR1 (200 μg/mouse 3×/week) for the duration of the experiment (50 days).

Clinical evaluation. Mice will be scored four times per week as follows: 0, no detectable signs of EAE; 0.5, limp distal tail; 1, complete limp tail; 1.5, limp tail and hind limb weakness; 2, unilateral partial hind limb paralysis; 2.5, bilateral partial hind limb paralysis; 3, complete bilateral hind limb paralysis; 3.5, complete hind limb paralysis and unilateral forelimb paralysis; 4, total paralysis of both fore-limbs and hind limbs; 5, death. Mice scoring greater than 4 but less than 5 will be euthanized.

Determination of Toxicity

A desired antibody according to the invention will have greatly reduced or no toxicity in the disclosed thrombotic animal model. Using the models described above, it will be shown that IgG1 anti-CD154 antibodies wherein the heavy chain of the constant regions contains E269R mutation and a K322A mutations (according to Kabat numbering scheme) do not elicit platelet aggregation Determination of Efficacy Efficacy (induction of tolerance) may be assessed in the skin graft tolerance models as afore-described.

Pharmaceutical and Diagnostic Uses of Inventive Anti-hCD154 Antibody

In one embodiment of this invention, an anti-CD154 antibody, or a pharmaceutical composition comprising the antibody, is capable of inhibiting an immune response in a subject. The antibody of this invention, or pharmaceutical composition of the invention, is administered to the subject in an effective inhibiting amount.

In certain embodiments, an "effective inhibiting amount" of an anti-CD154 antibody, or pharmaceutical composition comprising the antibody, is any amount which is effective to inhibit the CD154-CD40 interaction in the subject to whom it is administered. Methods of determining an "inhibiting amount" are well known to those skilled in the art and depend upon factors including, but not limited to: the type of subject involved, the size and age of the subject and the pharmacokinetic properties of the particular therapeutic agent delivered.

In another specific embodiment of this invention, an anti-CD154 antibody of this invention, or a pharmaceutical composition comprising the antibody, is capable of inhibiting the immune response by inhibiting the CD154-CD40 interaction.

In one embodiment of this invention, an anti-CD154 antibody of this invention, or a pharmaceutical composition comprising the antibody, is capable of inhibiting inflammation. For the purposes of this invention, inflammatory responses are characterized by redness, swelling, heat and pain, as consequences of capillary dilation with edema and migration of phagocytic leukocytes. Some examples of inflammatory responses include: arthritis, contact dermatitis, hyper-IgE syndrome, inflammatory bowel disease, allergic asthma, and idiopathic inflammatory disease. Idiopathic inflammatory disease includes, for example, psoriasis and lupus (e.g., systemic lupus erythematosus (SLE), drug-induced lupus erythematosus, and lupus nephritis). See, e.g., Gallin 1989. *Fundamental Immunology*, Chapter 26, Raven Press, 2d Ed., pp. 721-733, New York. This invention provides a method of treating or preventing a symptom of systemic lupus erythematosus (SLE) in an individual, the method comprising administering an anti-CD154 antibody of this invention, to an individual in an amount effective to treat or prevent a symptom of SLE.

Some examples of arthritis include: rheumatoid arthritis, non-rheumatoid inflammatory arthritis, arthritis associated with Lyme disease and inflammatory osteoarthritis. Some examples of idiopathic inflammatory disease include: psoriasis and systemic lupus. In one embodiment of this invention, an anti-CD154 antibody, or a pharmaceutical composition comprising the antibody, is capable of inhibiting rejection by the subject of a transplanted organ.

In a more specific embodiment of this invention, an anti-CD154 antibody of this invention, or a pharmaceutical composition comprising the antibody, is capable of inhibiting rejection by the subject of a transplanted heart, kidney, liver, skin, pancreatic islet cells or bone marrow.

In one embodiment of this invention, an anti-CD154 antibody of this invention, or a pharmaceutical composition comprising the antibody, is capable of inhibiting graft-vs-host disease in a subject.

In one embodiment of this invention, an anti-CD154 antibody of this invention, or a pharmaceutical composition comprising the antibody, is capable of inhibiting allergic responses, in a subject—for example, hay fever or an allergy to penicillin or other drugs.

In one aspect the subject anti-CD154 antibodies including INX021 are useful for alleviating or preventing anti-drug reactions, particularly those against biologics and other drugs such as therapeutic antibodies, fusion proteins, hormones, growth factors, enzymes, peptides, antibiotics, antivirals, and the like. This may enable these drugs to be administered for more prolonged duration, may increase the number of patients who respond to the drug, and/or may facilitate the efficacy of the drug intreated patients. Examples thereof are known in the art include Humira, Enbrel, Rituxan, Xolair, Herceptin, and Avastin.

Other examples of therapeutic antibodies wherein the subject anti-CD154 antibodies may be used to prevent or alleviate an anti-drug response against include the following: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pego, ALD518, Alemtuzumab, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab (=tocilizumab), Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brentuximab vedotin, Briakinumab, Brodalumab, Brolucizumab, Brontictuzumab, Cabiralizumab Canakinumab, Cantuzumab mertansine, Cantuzumab ravtansine Caplacizumab, Capromab pendetide Carlumab Carotuximab, Catumaxomab, CBR96-doxorubicin immunoconjugate, Cedelizumab, Cergutuzumab amunaleukin, Certolizumab pegol, Cetuximab, Ch. 14.18, Citatuzumab bogatox, Cixutumumab, Clazakizumab, Clenoliximab, Clivatuzumab tetraxetan, Codrituzumab, Coltuximab ravtansine, Conatumumab, Concizumab, Crenezumab, Crotedumab, CR6261, Dacetuzumab, Daclizumab, Dalotuzumab, Dapirolizumab pegol, Daratumumab, Dectrekumab, Demcizumab, Denintuzumab mafodotin, Denosumab, Derlotuximab biotin, Detumomab, Dinutuximab, Diridavumab, Dapirolizumab pegol, Daratumumab, Dectrekumab, Demcizumab, Denintuzumab mafodotin, Denosumab, Derlotuximab biotin, Detumomab Dinutuximab, Diridavumab Domagrozumab, Dorlimomab aritox, Drozitumab, Duligotumab Dupilumab Durvalumab Dusigitumab, Ecromeximab, Eculizumab, Edobacomab, Edrecolomab, Efalizumab, Efungumab, Eldelumab, Elgemtumab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Ensituximab, Epitumomab cituxetan, Epratuzumab, Erlizumab, Ertumaxomab, Etaracizumab, Etrolizumab, Evinacumab, Evolocumab, Exbivirumab, Fanolesomab, Faralimomab, Farletuzumab FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab, ozogamicin, Gevokizumab, Girentuximab, Glembatumumab, vedotin, Golimu, Gomiliximab, Guselkumab, Ibalizumab, Ibritumomab tiuxetan, Icrucumab, Idarucizumab, Igovomab, 1MAB362, lmalumab, Imciromab, lmgatuzumab, Inclacumab, Indatuximab ravtansine, Indusatumab vedotin, Inebilizumab, Infliximab, Intetumumab, Inolimomab, Inotuzumab ozogamicin, Ipilimumab, Iratumumab, Isatuximab, Itolizumab, Ixekizumab, Keliximab, Labetuzumab, Lambrolizumab, Lampalizumab, Lanadelumab, Laprituximab emtansine, Lebrikizumab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Mapatumumab, Margetuximab, Maslimomab, Mavrilimumab, Matuzumab, Mepolizumab, Metelimumab, Milatuzumab, Minretumomab, Mirvetuximab, soravtansine, Mitumomab, Mogamulizumab, Monalizumab, Morolimumab, Motavizumab, Moxetumomab pasudotox, Muromonab-CD3, Nacolomab tafenatox Namilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nimotuzumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Perakizumab, Pertuzumab, Pexelizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Teprotumumab, Tesidolumab, Tetulomab, Tezepelumab, TGN1412, Ticilimumab (tremelimumab), Tildrakizumab, Tigatuzumab, Timolumab, Tisotumab vedotin, TNX-650, Tocilizumab (atlizumab), Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Vadastuximab talirine, Vandortuzumab, Vedotin, Vantictumab, Vanucizumab, Vapaliximab, Varlilumab, Vatelizumab, Vepalimomab, Vesencumab, Visilizumab, Vobarilizumab, Volociximab, Vorsetuzumab, mafodotin, Votumumab, Xentuzumab, Zalutumumab, Zanolimumab, Zatuximab, Ziralimumab and Zolimomab aritox.

In one embodiment of this invention, an anti-CD154 antibody of this invention, or a pharmaceutical composition comprising the antibody, is capable of inhibiting the autoimmune response in subject suffering from autoimmune disease. In some embodiments, the autoimmune response is associated with or is derived from a condition selected from the group consisting of: rheumatoid arthritis, Myasthenia gravis, systemic lupus erythematosus, Graves' disease, idiopathic thrombocytopenia purpura, hemolytic anemia, diabetes mellitus, inflammatory bowel disease, Crohn's disease, multiple sclerosis, psoriasis, drug-induced autoimmune diseases, or drug-induced lupus. In certain embodiments, the autoimmune response is associated with or derived from systemic lupus erythematosus.

In one embodiment of this invention, an anti-CD154 antibody of this invention, or a pharmaceutical composition comprising the antibody, is capable of inhibiting an autoimmune response in a subject suffering from an autoimmune response which is derived from an infectious disease.

In one embodiment of this invention, an anti-CD154 antibody of this invention, or a pharmaceutical composition comprising the antibody, is capable of inhibiting an autoimmune response in a subject suffering from an autoimmune response which is derived from Reiter's syndrome, spondyloarthritis, Lyme disease, HIV infection, syphilis, or tuberculosis.

In one embodiment of this invention, an anti-CD154 antibody of this invention, or a pharmaceutical composition comprising the antibody, is capable of inhibiting fibrosis in a subject.

Some examples of fibrosis include: pulmonary fibrosis or fibrotic disease. Some examples of pulmonary fibrosis include: pulmonary fibrosis secondary to adult respiratory distress syndrome, drug-induced pulmonary fibrosis, idiopathic pulmonary fibrosis, or hypersensitivity pneumonitis. Some examples of fibrotic diseases include: Hepatitis-C; Hepatitis-B; cirrhosis; cirrhosis of the liver secondary to a toxic insult; cirrhosis of the liver secondary to drugs; cirrhosis of the liver secondary to a viral infection; and cirrhosis of the liver secondary to an autoimmune disease.

In one embodiment of this invention, an anti-CD154 antibody of this invention, or a pharmaceutical composition comprising the antibody, is capable of inhibiting gastrointestinal disease. Some examples of gastrointestinal disease include: esophageal dysmotility, inflammatory bowel disease (including Crohn's disease and ulcerative colitis), gastritis, collagenous colitis (including lymphocytic colitis and microscopic colitis), coeliac disease (also called gluten enteropathy, coeliac sprue, or gluten intolerance), and scleroderma.

In one embodiment of this invention, an anti-CD154 antibody of this invention, or a pharmaceutical composition comprising the antibody, is capable of inhibiting vascular disease. Some examples of vascular disease include: atherosclerosis, renal artery disease, lymphedema, ischemic disorders, and reperfusion injury. Also included are collagen vascular/immune complex diseases such as systemic lupus erythematosus or cryoglobulinemia.

In one embodiment of this invention, an anti-CD154 antibody of this invention, or a pharmaceutical composition comprising the antibody, is capable of inhibiting the proliferation of T cell tumor cells in a subject suffering from a T cell cancer, —e.g., a T cell leukemia or lymphoma. Such an anti-CD154 antibody, or a pharmaceutical composition comprising the antibody, may be administered to the subject in an amount effective to inhibit the proliferation of T cell tumor cells in that subject.

In one embodiment of this invention, an anti-CD154 antibody of this invention, or a pharmaceutical composition comprising the antibody, is capable of inhibiting viral infection of the T cells of a subject by the human T-cell lymphotropic virus type I (HTLV I). Such an anti-CD154 antibody or a pharmaceutical composition comprising the antibody may be administered to the subject in an amount effective to inhibit viral infection.

In one embodiment of this invention, an anti-CD154 antibody of this invention, or a pharmaceutical composition comprising the antibody, is capable imaging tumor cells or neoplastic cells in a subject that express a CD154 protein to which the antibody of this invention specifically binds. A method for imaging tumor cells or neoplastic cells in a subject comprises the steps of: administering to the subject an effective amount of an anti-CD154 antibody of this invention, or a composition comprising it, under conditions permitting the formation of a complex between the antibody and a protein on the surface of tumor cells or neoplastic cells; and imaging any antibody/protein complex formed, thereby imaging any tumor cells or neoplastic cells in the subject.

In one embodiment of this invention, an anti-CD154 antibody of this invention, or a pharmaceutical composition comprising the antibody, is capable of detecting the presence of tumor cells or neoplastic cells in a subject that express a CD154 protein to which the antibody of this invention specifically binds. One such method for detecting the presence of tumor cells or neoplastic cells in a subject comprises the steps of: administering to the subject an effective amount of an anti-CD154 antibody of this invention, or a pharmaceutical composition comprising it, under conditions permitting the formation of a complex between the antibody and a protein; clearing any unbound imaging agent from the subject; and detecting the presence of any antibody/protein complex formed, the presence of such complex indicating the presence of tumor cells or neoplastic cells in the subject.

Pharmaceutical Compositions

This invention provides pharmaceutical compositions comprising a CD154 binding protein, e.g., an anti-CD154 antibody, as described in this invention.

In one embodiment of this invention, the pharmaceutical composition comprises at least one anti-CD154 antibody, of this invention.

The inventive anti-CD154 antibodies or pharmaceutical composition comprising the antibody, do not cause thrombosis, including thromboembolic events and therefore are well suited for human therapy.

Such pharmaceutical compositions may further comprise any one or more of a pharmaceutically acceptable carrier, an adjuvant, a delivery vehicle, a buffer and/or a stabilizer. Exemplary techniques for formulation and administration of the antibodies of the present invention may be found, for example, in "Remington's Pharmaceutical Sciences," Mack Publishing Co., Easton, Pa., latest edition.

In a more particular embodiment of this invention, the pharmaceutically acceptable carrier is phosphate buffered saline, physiological saline, water, citrate/sucrose/Tween formulations and emulsions—e.g., oil/water emulsions.

In one embodiment of this invention, the pharmaceutical composition may be delivered in a microencapsulation device so as to reduce or prevent a host immune response against the composition. The binding agents, such as antibodies or antibody fragments of this invention, may also be delivered microencapsulated in a membrane, such as, for example, a liposome or other encapsulated or immunoprotected delivery vehicle.

In one embodiment of this invention, the pharmaceutical composition may be in the form of a sterile injectable preparation, for example, a sterile injectable aqueous or oleaginous suspension. This suspension may be formulated according to techniques known in the art using suitable dispersing, wetting, and suspending agents.

In one embodiment of this invention, the pharmaceutical composition may be delivered orally, topically or intravenously. When administered systemically, the therapeutic composition should be sterile, substantially pyrogen-free and in a parenterally acceptable solution having due regard for pH, isotonicity, and stability. For example, a pharmaceutical preparation is substantially free of pyrogenic materials so as to be suitable for administration as a human therapeutic. These conditions are known to those skilled in the art.

In a more specific embodiment of this invention, for oral administration, the pharmaceutical composition is formulated in a suitable capsule, tablet, aqueous suspension or solution. Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™), hydroxypropyl methylcellulose, sucrose, starch, and ethylcellulose. Lubricants that can be used include magnesium stearates, stearic acid, silicone fluid, talc, waxes, oils, and colloidal silica.

In a more specific embodiment of this invention, for topical applications, the pharmaceutical compositions may be formulated in a suitable ointment. Some examples of formulations of a composition for topical use include: drops, tinctures, lotions, creams, solutions, and ointments containing the active ingredient and various supports and vehicles.

In one embodiment of this invention, a topical semi-solid ointment formulation typically comprises a concentration of the active ingredient from about 1 to 20%, —e.g., 5 to 10%, in a carrier, such as a pharmaceutical cream base.

In one embodiment of this invention, pharmaceutical compositions for inhalation and transdermal compositions can also readily be prepared. The therapeutic composition can be administered through the nose or lung, for example, as a liquid or powder aerosol (lyophilized).

In one embodiment of this invention, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions of this invention can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In one embodiment of this invention, liquid formulations of a pharmaceutical composition for injection can comprise various carriers such as vegetable oils, dimethylacetamide, dimethylformamide, ethyl lactate, ethyl carbonate, isopropyl myristate, ethanol, polyols—i.e., glycerol, propylene glycol, liquid polyethylene glycol, and the like. In some embodiments, the composition includes a citrate/sucrose/Tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid—e.g., ethyl oleate.

In one embodiment of this invention, the pharmaceutical composition comprises from about 0.1 to 90% by weight (such as 1 to 20% or 1 to 10%) of an anti-CD154 antibody of this invention, in a pharmaceutically acceptable carrier.

In one embodiment of this invention, the optimal percentage of the anti-CD154 antibody of this invention in each pharmaceutical composition varies according to the formulation itself and the therapeutic effect desired in the specific pathologies and correlated therapeutic regimens. Pharmaceutical formulation is well-established in the art. Conventional methods, known to those of ordinary skill in the art of medicine, can be used to administer the pharmaceutical composition to the subject.

Accordingly, pharmaceutical compositions of the present invention relate to extended release formulations. Extended release, or controlled release or slow release, refers to drug formulations that release active drug, such as a polypeptide or antibody drug, over a period of time following administration to a subject. Extended release of polypeptide drugs, which can occur over a range of desired times (e.g., minutes, hours, days, weeks or longer, depending upon the drug formulation) differs from standard formulations in which substantially the entire dosage unit is available for immediate absorption or immediate distribution via the blood-stream. Extended release formulations may, in certain embodiments, result in a level of circulating drug from a single administration that is sustained, for example, for 8 hours or more, 12 hours or more, 24 hours or more, 36 hours or more, 48 hours or more, 60 hours or more, 72 hours or more 84 hours or more, 96 hours or more, or even, for example, for 1 week or 2 weeks or more, for example, 1 month or more. Extended release compositions may comprise an anti-CD154 antibody of the present invention.

In some embodiments of this invention, the pharmaceutical composition further comprises another immunosuppressive or immunomodulatory compound. For example, such an immunosuppressive or immunomodulatory compound may be one of the following: an agent that interrupts T cell costimulatory signaling via CD28; an agent that interrupts calcineurin signaling, a corticosteroid, an anti-proliferative agent, and an antibody that specifically binds to a protein expressed on the surface of immune cells, including but not limited to CD45, CD2, IL2R, CD4, CD8 and RANK FcR, B7, CTLA4, TNF, LTβ and VLA-4.

In a some embodiments of this invention, the immunosuppressive or immunomodulatory compound is tacrolimus, sirolimus, mycophenolate mofetil or its active form mycophenolic acid, mizoribine, deoxyspergualin, brequinar sodium, leflunomide, rapamycin or azaspirane.

In other embodiments of this invention, antibodies of this invention or pharmaceutical compositions comprising them may be included in a container, package or dispenser alone or as part of a kit with labels and instructions for administration.

Administration and Delivery Routes

The anti-CD154 antibodies of this invention and pharmaceutical compositions of this invention may be administered to a subject in any manner which is medically acceptable. For the purposes of this invention, "administration" means any of the standard methods of administering an antibody, antibody fragment or pharmaceutical composition known to those skilled in the art, and should not be limited to the examples provide herein.

In some embodiments of this invention, the anti-CD154 antibodies of this invention and pharmaceutical compositions of this invention may be administered to a subject by injection intravenously, subcutaneously, intraperitoneally, intramuscularly, intramedullarily, intraventricularly, intra-epidurally, intraarterially, intravascularly, intra-articularly, intra-synovially, intrastemally, intrathecally, intrahepatically, intraspinally, intratumorally, intracranially; by enteral, intrapulmonary, transmucosal, intrauterine, or sublingual routes of administration, or locally, e.g., at sites of inflammation or tumor growth.

In some embodiments of this invention, the anti-CD154 antibodies of this invention and pharmaceutical compositions of this invention may be administered to a subject orally or nasally, or by inhalation, ophthalmic, rectal, or topical routes.

In a more specific embodiment, the anti-CD154 antibodies of this invention, and pharmaceutical compositions of this invention may be administered to a subject orally in the form of capsules, tablets, aqueous suspensions or solutions.

In a more specific embodiment, the anti-CD154 antibodies of this invention and pharmaceutical compositions of this invention may be administered to a subject topically by application of a cream, ointment or the like.

In other embodiments of this invention, the anti-CD154 antibodies of this invention, and pharmaceutical compositions of this invention may also be administered by inhalation through the use of a nebulizer, a dry powder inhaler or a metered dose inhaler.

In further embodiments of this invention, the anti-CD154 antibodies of this invention, and pharmaceutical compositions of this invention may be administered to a subject by sustained release administration, by such means as depot injections of erodible implants directly applied during surgery or by implantation of an infusion pump or a biocompatible sustained release implant into the subject.

In a more specific embodiment, the anti-CD154 antibodies of this invention, and pharmaceutical compositions of this invention may be administered to a subject by injectable depot routes of administration, such as by using 1-, 3-, or 6-month depot injectable or biodegradable materials and methods.

In a more specific embodiment, the anti-CD154 antibodies of this invention, and pharmaceutical compositions of this invention may be administered to a subject by applying to the skin of the subject a transdermal patch containing the antibody, antibody derivative or pharmaceutical composition, and leaving the patch in contact with the subject's skin, generally for 1 to 5 hours per patch.

In other embodiments of this invention, the anti-CD154 antibodies of this invention, and pharmaceutical compositions of this invention may be administered to a subject at any dose per body weight and any dosage frequency that is medically acceptable. Acceptable dosage includes a range of between about 0.01 and 200 mg/kg subject body weight.

The subject anti-CD154 antibodies are administered to a subject in an amount effective to elicit a desired effect on immunity, i.e., suppression of T or B cell immunity, or an amount effective to prevent, treat or ameliorate the symptoms of a disease wherein the suppression of B or T cell immunity is therapeutically desired. As mentioned these conditions include in particular autoimmune, inflammatory and allergic indications.

The total administered dosage of the antibody alternatively may comprise from 0.01, 0.1, 1, 5, 10, 15, 20, 25, 50, 100 or more mg or may comprise any amount intervening the foregoing mg values. In a preferred embodiment of the invention, the anti-CD154 antibodies described herein, or binding fragments thereof, as well as combinations of said antibody fragments, may be administered to a recipient subject with a frequency of once every twenty-six weeks or less, such as once every sixteen weeks or less, once every eight weeks or less, or once every four weeks, monthly, biweekly or less.

In any of the methods of using the antibodies or pharmaceutical compositions of this invention, the antibodies or pharmaceutical compositions may be administered to a subject in single or multiple doses daily, every 2, 3, 4, 5 or 6 days, weekly, monthly or any fraction or multiple thereof, and further may be administered to a subject repeatedly at intervals ranging from each day to every other month, as determined by the skilled practitioner.

In any of the methods of using the antibodies or pharmaceutical compositions of this invention, the antibodies or pharmaceutical compositions comprising them, may be administered to a subject in need thereof at intervals for as long a time as medically indicated, ranging from days or weeks to the life of the subject. In further embodiments, the anti-CD154 antibodies of this invention, and pharmaceutical compositions of this invention may be administered to a subject repeatedly at intervals ranging from each day to every other month.

In one embodiment of this invention, the anti-CD154 antibodies of this invention, and pharmaceutical compositions of this invention can be administered in multiple doses per day, if desired, to achieve the total desired daily dose. The effectiveness of the method of treatment can be assessed by monitoring the subject for known signs or symptoms of a disorder.

For all embodiments of this invention, the dosage and dose rate of the anti-CD154 antibodies of this invention and pharmaceutical compositions of this invention effective to produce the desired effects will depend on a variety of factors, such as the nature of the disease to be treated, the size and age of the subject, the goal of the treatment, the specific pharmaceutical composition used, the pharmacokinetics of the active agent, and the judgment of the treating physician.

It is understood that the effective dosage may depend on recipient subject attributes, such as, for example, age, gender, pregnancy status, body mass index, lean body mass, condition or conditions for which the composition is given, other health conditions of the recipient subject that may affect metabolism or tolerance of the composition, levels of IL-6 in the recipient subject, and resistance to the composition (for example, arising from the patient developing antibodies against the composition). A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

Accordingly, anti-CD154 antibodies of this invention, and pharmaceutical compositions of this invention, will be administered in an amount effective to achieve their intended purpose. A therapeutically effective amount may refer to an amount of antibody effective to prevent, alleviate or ameliorate symptoms of disease or prolong the survival of the subject being treated. A therapeutically effective amount may be achieved by altering the dose and dosing schedule of administration of the subject antibodies.

The anti-CD154 antibodies of this invention, and pharmaceutical compositions of this invention may be administered as a single dosage for certain indications, such as preventing immune response to an antigen to which a subject is exposed for a brief time, such as an exogenous antigen administered on a single day of treatment. Examples of such a therapy would include coadministration of the antibody fragment of the invention along with a therapeutic agent, for example an antigenic pharmaceutical, an allergen or a blood product, or a gene therapy vector. In indications where antigen is chronically present, such as in controlling immune reaction to transplanted tissue or to chronically administered antigenic pharmaceuticals, the antibody fragments or pharmaceutical compositions of the invention are administered at intervals for as long a time as medically indicated, ranging from days or weeks to the life of the subject.

In any of the methods described herein, the antibodies or pharmaceutical compositions may be administered to a subject with a second agent. In certain embodiments, the agent is a therapeutic agent, such as, for example, an immunomodulatory or immunosuppressive agent. The immunomodulatory or immunosuppressive agent may be any of the following:

(a) an agent that interrupts T cell costimulatory signaling via CD28;

(b) an agent that interrupts calcineurin signaling, (c) a corticosteroid, (d) an anti-proliferative agent; and (e) an antibody that specifically binds to a protein expressed on the surface of immune cells, including but not limited to CD45, CD2, IL2R, CD4, CD8 and RANK FcR, B7, CTLA4, TNF, LTβ and VLA-4.

The immunosuppressive or immunomodulatory compound may be, for example, tacrolimus, sirolimus, mycophenolate mofetil, mizoribine, deoxyspergualin, brequinar sodium, leflunomide, rapamycin or azaspirane. The antibody and second agent may be administered simultaneously or sequentially. In some instances, it may be advantageous to administer one or more nucleic acids of the invention to a subject in need thereof. Therapeutic and diagnostic methods of the invention comprising the step of administering at least one nucleic acid of the invention according to well-known methods are included in the scope of the present invention.

In one embodiment of this invention, the subject(s) that can be treated by the above-described methods is an animal. Preferably, the animal is a mammal. Examples of mammals that may be treated include, but are not limited to, humans, non-human primates, rodents (including rats, mice, hamsters and guinea pigs) cows, horses, sheep, goats, pigs, dogs and cats. Preferably, the mammal is a human.

This invention may be better understood based on the Examples that follow. However, one skilled in the art will readily appreciate that the specific methods and results discussed are merely illustrative of the invention as described herein.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Design of Antibody Variants with Higher Affinity to Human CD154 (Lower $K_D$ Values)

In this application the present inventors describe a novel humanized anti-human CD154 IgG1 antibody having the sequences contained in FIGS. 1A-C which is for use in human therapy, particularly therapeutic indications wherein suppression of T and B cell immunity is therapeutically desirable. As afore-stated this antibody was derived from IDEC131 by the combined use of affinity maturation and mutagenesis methods and by the modification of the IgG1 Fc region of IDEC-131 in order to eliminate FcγRII and FcγRIIII and C1q (complement binding).

Particularly, various combinations of CDR residues in both the heavy and light variable regions of IDEC131 were mutated with the objective of obtaining a variant of IDEC-131 having improved binding affinity to human CD154.

These experiments resulted in a large number of variants. The overwhelming number of these variants did not bind to human CD154 better than IDEC-131, rather they had the same or worse binding affinities to human CD154 (results not shown).

These experiments resulted in 11 humanized variants which are identified in and which contain the variable light and heavy chain sequences shown FIGS. 2A-2C and 3. The sequences of the heavy and light variable sequences of these variants which are identified in this application as variant 21, variant 22, variant 23, variant 24, variant 25, variant 26, variant 27, variant 28, variant 29, variant 30 and variant 31 are contained in FIG. 2.

Table 4 summarizes the different binding affinities of these variants as determined by Biacore.

TABLE 4

| Variant* | $K_a$(1/Ms) | $K_d$ (1/s) | $K_D$ | Chi$^2$ | Fold improvement in $K_D$ (compared to IDEC131) |
|---|---|---|---|---|---|
| IDEC-131 | 3.468E+06 | 5.25E−04 | 1.51E−10 | 0.097 | 1.0 |
| 21 | 4.42E+06 | 1.28E−04 | 2.89E−11 | 0.184 | 4.7 |
| 22 | 4.48E+06 | 1.17E−04 | 2.62E−11 | 0.222 | 5.2 |
| 23 | 3.35E+06 | 1.41E−04 | 4.21E−11 | 0.242 | 4.2 |
| 24 | 3.70E+06 | 1.35E−04 | 3.64E−11 | 0.265 | 4.9 |
| 25 | 4.11E+06 | 1.49E+04 | 3.62E−11 | 0.243 | 3.9 |
| 26 | 2.03E+06 | 1.17+04 | 5.76E−11 | 0.201 | 2.5 |
| 27 | 3.58E+06 | 1.20E−04 | 3.36E−11 | 0.135 | 4.5 |
| 28 | 3.65E+06 | 1.15E−04 | 3.15E−11 | 0.108 | 4.8 |
| 29 | 3.86E+06 | 1.33E−04 | 3.44E−11 | 0.152 | 4.2 |
| 30 | 4.24E+06 | 1.40E−04 | 3.29E−11 | 0.171 | 4.4 |
| 31 | 3.61E+06 | 1.23E−04 | 3.41E−11 | 0.121 | 4.8 |

*(Average n = 6)

binding affinity of each of these variants to human CD154 was then screened by Biacore. The Biacore assay was conducted as shown below.

Biacore Assay:

Equipment: Biacore 3000

Assay Buffer—10 nM HEPES buffer (pH 7.4), 150 nM NaCl, 3 mM EDTA, 0.05% P20 (polyoxyethylenesorbitan)

Regeneration buffer—10 mM Glycine HCl (pH 1.75)

Conjugation Buffer—10 nM sodium acetate buffer (pH 5)

Flow Rate—Flow rate for ligand capture is 5 μl/min. The flow rate for kinetic analysis is 30 μl/min.

Procedures:

Binding experiments were performed on Biacore 300 at 25° C. Antibodies were directly immobilized on flow cell 2 (1000 RU of combination #23) and flow cell 4 (1000 RU of EWT #131) and CD154 antigen was flowed over the chip. Binding of antigen to the tested antibodies was monitored in real time. From the observed $k_{on}$, the $k_{off}$ and $K_D$ was determined for each variant.

Scoring analysis was performed using specific analyte concentrations. At the tested concentration, binding should be observed even if the ligand binding affinity is relatively weak. Full kinetics may be performed by known methods. For the molecular interactions with fast off rate, steady state kinetics may be used to determine the KD value.

Chi square ($\chi 2$) analysis may be carried out to determine the accuracy of the analysis. An $\chi 2$ within 1-2 is considered significant and below 1 is considered highly significant. This screen resulted in the identification of a number of sequence variants with significantly improved binding affinities, i.e., 4-5-fold better relative to IDEC-131. As noted previously this outcome was much unexpected as IDEC-131 possesses a binding affinity or KD of 151 pm. This result was further surprising since IDEC-131 was selected as the lead clinical candidate from among a number of different candidate humanized sequences based on its potent binding affinity for CD154.

As shown below humanized anti-CD154 antibodies derived from IDEC-131 were obtained which had $K_D$ values ranging from as low as 26 pm to 57 pm. The amino acid Example 2: Use of Antibody Variants with Higher Affinity to Human CD154 (Lower $R_D$ Values) for SC Administration As shown in the Table above, the variant selected as the lead candidate #21 has a $K_D$ value of 29 pM which is 4.7-fold better than IDEC131. This affinity improvement is significant as it should allow for this antibody to be administered subcutaneously. Previous studies with IDEC131 have shown human clinical efficacy at above 10 mg/kg, or for the purposes of analysis an upper limit of 20 mg/kg. Based thereon, and assuming a person of average weight of about 80 kg, a dose effective amount may be calculated as follows: 10 mg/kg×80 kg=800 mg dose.

However, an antibody formulation for s use customarily does not exceed 100 ng/ml. (http://www.sciencedirect.com/science/article/pii/S0169409X06000895)

Moreover, a typical tolerated dose volume for s.q. administration ranges from about 0.5-5 ml (volumes larger than 3 mL are considered "large"). Therefore, an effective dosage for IDEC-131 would require about 8 mL. (see calculation below.) This dosage volume well exceeds s.q. medical norms.

(10 mg/kg×80 kg)/100 mg/ml=8 mL.

By contrast, since the variant #21 (INX021) has a $K_D$ which is about 5-fold less (i.e., binds with greater affinity to CD154) the variant would require 5-fold less drug to achieve the same efficacy. As shown below this would translate into a dosage volume of about 1.6 ml which is well with the level of medical conventions for s.q. injections for patients.

(2 mg/kg×80 kg)/100 mg/ml=1.6 mL.

Therefore, unlike IDEC131, INX021 should be well suited for administration via s.q. routes.

Example 3: Comparison of Potency of Anti-CD154 Antibodies According to the Invention FIG. 4 depicts schematically the results of experiments detecting inhibition of T cell CD154-driven B cell activation. These results contained in the Figure demonstrate the improved potency, i.e., greater inhibition of T cell CD154-driven B cell activation of INX-021 as compared to IDEC-131.

Example 4: Ability of Inventive Antibody to Elicit Tolerance

FIG. 5 shows the results of experiments demonstrating that anti-mouse CD154 IgG1 antibodies containing the same Fc mutations as are contained in INX021 (E269R and K322A)) are able to induce tolerance in the skin test previously described. Therefore, anti-human CD154 antibodies containing these mutated IgG1 constant regions should elicit tolerance and block the other effects of CD154 in human patients.

Example 6: INX021 does not Elicit Platelet Aggregation In Vitro

FIG. 6 shows the results of experiments which revealed that the INX021 antibody containing mutations which reduce or eliminate FcR binding does not induce platelet aggregation in vitro in an assay using immune complexes of the subject INX021 antibody and collagen. These in vitro experiments revealed that immune complexes of FcR mutants over a 16 or 20 minute period did not induce the activation or aggregation of either isolated mouse or human platelets. By contrast in the same assay the control 5c8 antibody caused platelet aggregation.

Example 7: Anti-CD154 Antibodies According to the Invention do not Elicit Platelet Aggregation In Vivo FIG. 7A-D shows the results of experiments demonstrating that that INX021 does not activate platelets, does not induce platelet aggregation and does not affect (reduce) platelet numbers in vivo. The experiment in FIG. 7A shows that INX021 does not induce thrombotic stress or activate platelets as compared to the positive control. The experiment in FIG. 7B shows that INX021 does not affect the numbers of circulating platelets as compared to the positive control. The experiment in FIG. 7C shows that INX021 does not elicit the formation of clots (emboli) in the lung as compared to the positive control. FIG. 7D summarizes the benefits of INX021 in vivo, i.e., it does not reduce platelet numbers, it does not activate platelets, it does not cause platelet stress and it does not induce the formation of clots.

Example 8: Use of Anti-CD154 Antibodies According to the Invention in Autoimmunity Models The experiments summarized in FIG. 8A-B show that anti-humanized anti-CD154 IgG1 antibodies containing the Fc mutations in INX021 which reduce or eliminate FcR binding are active in different autoimmune or inflammatory models.

The experiment in FIG. 8A shows that human CD154 IgG1 antibodies containing the Fc mutations in INX021 potently suppress EAE over about a 20 day period. The experiment in FIG. 8B shows that humanized anti-CD154 IgG1 antibodies containing the Fc mutations in INX021 potently suppress humoral immunity against myelin oligo-dendrocyte glycoprotein ("MOG") comparably to the parent antibody.

Example 9: Testing of IDEC-131 Variants Including INX021 on their Ability to Suppress T Cell-Induced B Cell Activation The experiment in FIG. 9 compares the effects of different antibody variants according to the invention, i.e., variant #21 (TNX021)-#31 to suppress T cell-induced B cell activation based on CD86 expression. In these experiments the suppressive effects of antibody variants according to the invention was compared in a mixed lymphocyte reaction. The readout was CD86 expression by activated B cells. As shown in the Figure the antibodies with better $K_D$ values did not necessarily correlate to an improved functional effect in the MLR reactions. INX021 had superior immunosuppressive properties compared to other variants.

Example 10: INX021 Toxicology Study and T Cell Dependent Antibody Response (TDAR) Measurements In order to assess its suitability for use in human therapy the inventive antibody INX021 was examined in an 8 week non-GLP tox study in Rhesus monkeys at the CRL and Harvard facilities. The study design is shown in the tables below. The goals of the study were to assess the safety and efficacy of INX021 in a non-human primate (NHP).

TABLE 5

Overview of TDAR experiment:

| Overview of TDAR experiment: | |
| --- | --- |
| Dosing starts | Day 1 |
| $1^{st}$ KLH dose | Day 29 |
| Bleeds | Days 29, 36, 39 (Days post KLH dose 0, 7, 10) |
| $2^{nd}$ KLH dose | Day 43 |
| Bleeds | Days 43, 50, 53, 57 |
| | (Days post KLH dose 14, 21, 24, 28) |
| Measures IgG and IgM | |

TABLE 6

TDAR NHP groups:

| Site | Treatment | N | NHP species |
| --- | --- | --- | --- |
| CRL | Vehicle | 4 | Rhesus |
| CRL | INX021 50 mg/kg | 8 | Rhesus |
| CRL | 5C8 20 mg/kg | 8 | Rhesus |
| Harvard | Vehicle | 3 | Cynomolgus |
| Harvard | INX021 1 mg/kg | 3 | Cynomolgus |
| Harvard | INX021 5 mg/kg | 3 | Cynomolgus |

FIG. 10A-B compares the effects of INX021 and chimeric 5c8 antibody on the production of IgG and IgM antibodies in a KLH assay. FIG. 10A compares their effects on IgG's and FIG. 10B compares their effects on IgM's.

FIG. 11A-B compares the effects of vehicle, INX021 and 5c8 antibody on germinal center scores. FIG. 11A shows the germinal score comparison and FIG. 11B contains histograms comparing number and degree of cellularity of the germinal centers in spleens and lymph nodes (LNs) of treated animals.

FIG. 12 summarizes the observed lesion frequency to published results with another anti-CD154 antibody (Pegylated αCD154 Fab of Biogen/UCB).

These results indicate that INX021 should be safe and effective in human therapy.

35

Example 11: INX021 Suppresses Anti-Drug Antibody (ADA) Responses in NHPs

During the INX021 tox/TDAR experiments discussed in the prior example we measured the presence of ADAs in all cohorts. The TDAR responses in all animals were suppressed suggesting that antibody responses to soluble antigens could be prevented in INX021-treated animals. To examine this, we measured ADA responses in rhesus monkeys following 8 weeks of INX021, or 5C8 injections. All but one animal at the lowest doses (1 mg/kg) of the INX021 group failed to develop any detectable ADA.

Methods:

Detection of Antibodies Against INX021 and ch5C8 in Rhesus (ELISA)

Preparation of 2N Sulfuric Acid (Stop Solution)

For every 1000 mL of 2N sulfuric acid to be prepared combine 500 mL of 4N sulfuric acid with 500 mL of distilled water. Mix well. An expiration date of one year from the date of preparation or the manufacturer's expiration date for each of the individual components, whichever comes first, will be assigned. The solution will be stored at room temperature (17° C. to 27° C.).

Preparation of Coated 96-Well Plates

In these protocols the test material refers to samples containing Rhesus or Cynomolgus monkey serum, samples containing positive control, and/or blanks.

Protocol

1. Prepare a 1.0 μg/mL Coating Solution with INX021 or ch5C8 using Coating Buffer (0.2 Carbonate Bicarbonate Buffer) as the diluent.
2. Add 100 μL of the Coating Solution to each well of a 96-well clear polystyrene plate(s) and cover.
3. Incubate the plate(s) for 12 to 24 hours at 2° C. to 8° C.
4. Aspirate (remove) the Coating Solution from each well of the plate(s), then wash each well with 3×300 μL of 1×PBS-T.
5. Add 200 μL of Blocker Casein to each well of the plate(s) and cover.
6. Incubate the plate for 1 hour+5 minutes.
7. Aspirate Blocker Casein from each well of the plate(s), then wash each well with 3×300 μL of 1×PBS-T.
8. Use the plate(s) immediately after washing (complete plating within 2 hours from completion of washing). Assign an expiration date of the date plate preparation was completed.

Assay Procedure for Detection of Antibodies Against INX021 or ch5C8

In these experimental protocols the "test material" refers to samples containing Rhesus or Cynomolgus monkey serum, samples containing positive control, and/or blanks. Room/Ambient Temperature is 17° C. to 27° C.

Protocol

1. Add 100 μL of each test material to the appropriate well(s) of the INX021 or ch5C8 coated plate(s) and cover with plate sealer.
2. Use the plate template to record the placement of the test material.
3. Incubate the test material with the INX021 or ch5C8 coated plate(s) at room temperature for 1 hour+5 minutes.

Analytical Procedure

1. Aspirate the test material from each well of the plate(s), then wash each well of the plate(s) with 3×300 μL of 1×PBS-T.

2. Add 100 μL of 0.125 μg/mL INX021-BIOTIN or 1.0 μg/mL ch5C8-BIOTIN to each well of the plate(s) and cover with plate sealer.
3. Incubate the plate(s) at room temperature for 1 hour±5 minutes.
4. Aspirate (remove) the INX021-BIOTIN or ch5C8-BIOTIN from each well of the plate(s), then wash each well of the plate(s) with 3×300 μL of 1×PBS-T.
5. Add 100 μL of 0.1 μg/mL SA-HRP to each well of the plate(s) and cover.
6. Incubate the plate(s) at room temperature for 30 minutes±5 minutes.
7. Aspirate (remove) the SA-HRP from each well of the plate(s), then wash each well of the plate(s) with 3×300 μL of 1×PBS-T.
8. Add 100 μL of TMB to each well of the plate(s).
9. Incubate the plate(s) at room temperature for 20 minutes±5 minutes.
10. Add 100 μL of 2N Sulfuric Acid to each well of the plate(s).
11. Read the plate(s) at 450 nm using the microplate spectrophotometer within 30 minutes of analysis.

General Data Reduction

For all test material a mean A450, standard deviation, and % difference (if n=2) or CV % (if n>3) will be calculated to assess variance, unless otherwise stated. All CV % acceptance criteria will apply to the % difference values if % difference is calculated in lieu of CV %. If three or more wells of test material are analyzed one well may be omitted if the CV % does not pass the outlined criteria.

$$\% \text{ CV: } r \text{ Standard Deviation} > \text{Mean Value} \times 100$$

$$\% \text{ difference: } r \text{ Value } A - \text{Value } B \; v \; \text{Mean Value} \times 100$$

A Maximum Normed Residual (MNR) analysis will be performed to assess variance at the 5% level on the Blank TS to remove at most two outlier A450 Blank Test Samples (TS) values. A mean A450 will be calculated from all values not removed as outliers. Additional wells may be omitted due to technical error.

A plate specific cut point (PSCP) will be calculated as the overall Cut Point (CP)×Blank TS mean A450 (without outliers)=PSCP.

General Acceptance Criteria

If the Blank TS has more than two outliers the plate fails and should be re-analyzed. At least 5 Blank TS A450 values must remain for MNR analysis after masking outliers and wells that were masked due to technical error. The following equation will be used to calculate the MNR value: MNR Blank TS value×mean Blank TS Standard Deviation x Vn−1

The value will be determined to be an outlier if the MNR value is greater than the critical value. The critical values are defined as: n=12=0.727, n=11=0.745, n=10=0.763, n=9=0.783, n=8=0.804, n=7=0.825, n=6=0.844, and n=5=0.858. All outliers will be masked.

The Blocker Casein Blank and Blank TS mean A450 after outlier removal should be less than the LPC A«0. A Plate Specific Cut Point (PSCP) will be calculated as: PSCP=CF*Blank TS Global Mean (without outliers). Correction Factor (CF) will be added to the study file. The LPC mean A450 must be above the PSCP. If not, the LPC for that set fails.

The assay buffer blank CV % should be <30%. If the assay buffer blank does not pass the criteria listed above, the plate will be assessed during scientific review to determine if the data can be utilized.

The HPC>MPC>LPC for the mean A450 of each PC set. At least two-thirds of the PC levels must meet the acceptance criteria, with at least one PC at each PC level within the acceptance criteria.

Test Samples % difference between duplicate wells should be <25%. If a Test Sample does not pass these criteria, the sample will be reanalyzed.

Preparation of Positive Controls, Blank TS and Assay Buffer Blank

Positive controls will be prepared by spiking the surrogate positive control antibody in 100% Rhesus Monkey serum (RHS) or Cynomolgus Monkey serum. The positive controls in 100% matrix will be diluted 10-fold with Blocker Casein to yield the appropriate working concentration and 10% matrix. Each PC set will be prepared independently of one another and will be analyzed on each plate. On the day of analysis, the PCs will be analyzed on each plate.

Each plate will contain two sets of PCs LPC (50 ng/mL), MPC (250 ng/mL and HPC (1000 ng/mL). Blank TS will also be prepared with a final concentration of 10% matrix diluted with Blocker Casein. 12 wells of Blank TS will be run on each plate. Blocker Casein will be run in at least two wells on each plate. All test material will be analyzed in a minimum of two wells unless otherwise stated.

Screening Assay

For screening, samples are diluted 1/10 in Blocker Casein are analyzed per the procedure described in section 7.0. The mean absorbance value of study samples, during sample analysis, will be compared to the PSCP and will be reported as potentially positive if the mean absorbance value is >PSCP or negative if the mean absorbance value is <PSCP.

Results

The TDAR responses in all animals were suppressed suggesting that antibody responses to soluble antigens could be prevented in INX021-treated animals. To examine this, we measured ADA responses in rhesus monkeys following 8 weeks of INX021, or 5C8 injections. All but one animal at the lowest doses (1 mg/kg) of the INX021 group failed to develop any detectable ADA. Therefore, the inventive antibody INX021 may be used to suppress humoral immunity, e.g., against immunogenic drugs such as biologics, e.g., therapeutic antibodies, fusion proteins and the like.

REFERENCES CITED IN APPLICATION

The following references are cited. The contents of all are incorporated by reference herein.

1 Noelle, R. J., Mackey, M., Foy, T., Buhlmann, J. and Burns, C., CD40 and its ligand in autoimmunity. Ann N Y Acad Sci 1997. 815: 384-391.

2 Mackey, M. F., Barth, R. J., Jr. and Noelle, R. J., The role of CD40/CD154 interactions in the priming, differentiation, and effector function of helper and cytotoxic T cells. J Leukoc Biol 1998. 63: 418-428.

3 Noelle, R. J., CD40 and its ligand in cell-mediated immunity. Agents Actions Suppl 1998. 49: 17-22.

4 Quezada, S. A., Jarvinen, L. Z., Lind, E. F. and Noelle, R. J., CD40/CD154 Interactions at the Interface of Tolerance and Immunity. Annu Rev Immunol 2004. 22: 307-328.

5 Kenyon, N. S., Chatzipetrou, M., Masetti, M., Ranuncoli, A., Oliveira, M., Wagner, J. L., Kirk, A. D., Harlan, D. M., Burkly, L. C. and Ricordi, C., Long-term survival and function of intrahepatic islet allografts in rhesus monkeys treated with humanized anti-CD154. Proc Natl Acad Sci USA 1999. 96: 8132-8137.

6 Kirk, A. D., Burkly, L. C., Batty, D. S., Baumgartner, R. E., Berning, J. D., Buchanan, K., Fechner, J. H., Jr., Germond, R. L., Kampen, R. L., Patterson, N. B., Swanson, S. J., Tadaki, D. K., TenHoor, C. N., White, L., Knechtle, S. J. and Harlan, D. M., Treatment with humanized monoclonal antibody against CD154 prevents acute renal allograft rejection in nonhuman primates. Nat Med 1999. 5: 686-693.

7 Sidiropoulos, P. I. and Boumpas, D. T., Lessons learned from anti-CD40L treatment in systemic lupus erythematosus patients. Lupus 2004. 13: 391-397.

8 Sidiropoulos, P. I. and Boumpas, D. T., Lessons learned from anti-CD40L treatment in systemic lupus erythematosus patients. Lupus 2004. 13: 391-397.

9 Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., The contribution of Fc effector mechanisms in the efficacy of anti-CD154 immunotherapy depends on the nature of the immune challenge. Int Immunol 2004. 16: 1583-1594.

10 U.S. Pat. No. 6,444,018

11 Gordon, E. J., Markees, T. G., Phillips, N. E., Noelle, R. J., Shultz, L. D., Mordes, J. P., Rossini, A. A. and Greiner, D. L., Prolonged survival of rat islet and skin xenografts in mice treated with donor splenocytes and anti-CD154 monoclonal antibody. Diabetes 1998. 47: 1199-1206.

12 Markees, T. G., Phillips, N. E., Noelle, R. J., Shultz, L. D., Mordes, J. P., Greiner, D. L. and Rossini, A. A., Prolonged survival of mouse skin allografts in recipients treated with donor splenocytes and antibody to CD40 ligand. Transplantation 1997. 64: 329-335.

13 Jarvinen, L. Z., Blazar, B. R., Adeyi, O. A., Strom, T. B. and Noelle, R. J., CD154 on the surface of CD4+CD25+ regulatory T cells contributes to skin transplant tolerance. Transplantation 2003. 76: 1375-1379.

14 Quezada, S. A., Fuller, B., Jarvinen, L. Z., Gonzalez, M., Blazar, B. R., Rudensky, A. Y., Strom, T. B. and Noelle, R. J., Mechanisms of donor-specific transfusion tolerance: preemptive induction of clonal T-cell exhaustion via indirect presentation. Blood 2003. 102: 1920-1926.

15 Frleta, D., Lin, J. T., Quezada, S. A., Wade, T. K., Barth, R. J., Noelle, R. J. and Wade, W. F., Distinctive maturation of in vitro versus in vivo anti-CD40 mAb-matured dendritic cells in mice. J Immunother 2003. 26: 72-84.

16 Quezada, S., Eckert, M., Schned, A., Noelle, R. J. and Burns, C., Distinct mechanisms of action of anti-CD154 in early versus late treatment of murine lupus nephritis. Arth Rheum. 2003. in press.

17 Elster, E. A., Xu, H., Tadaki, D. K., Montgomery, S., Burkly, L. C., Berning, J. D., Baumgartner, R. E., Cruzata, F., Marx, R., Harlan, D. M. and Kirk, A. D., Treatment with the humanized CD154-specific monoclonal antibody, hu5C8, prevents acute rejection of primary skin allografts in nonhuman primates. Transplantation 2001. 72: 1473-1478.

18 Benda, B., Ljunggren, H. G., Peach, R., Sandberg, J. O. and Korsgren, O., Co-stimulatory molecules in islet xenotransplantation: CTLA4Ig treatment in CD40 ligand-deficient mice. Cell transplantation 2002. 11: 715-720.

19 Wekerle, T. and Sykes, M., Mixed chimerism and transplantation tolerance. Annual review of medicine 2001. 52: 353-370.

20 Camirand, G., Caron, N. J., Turgeon, N. A., Rossini, A. A. and Tremblay, J. P., Treatment with anti-CD154 antibody and donor-specific transfusion prevents acute rejection of myoblast transplantation. Transplantation 2002. 73: 453-461.

21 Tung, T. H., Mackinnon, S. E. and Mohanakumar, T., Long-term limb allograft survival using anti-CD40L antibody in a murine model. Transplantation 2003. 75: 644-650.

22 Koyama, I., Kawai, T., Andrews, D., Boskovic, S., Nadazdin, O., Wee, S. L., Sogawa, H., Wu, D. L., Smith, R. N., Colvin, R. B., Sachs, D. H. and Cosimi, A. B., Thrombophilia associated with anti-CD154 monoclonal antibody treatment and its prophylaxis in nonhuman primates. Transplantation 2004. 77: 460-462.

23 Kawai, T., Andrews, D., Colvin, R. B., Sachs, D. H. and Cosimi, A. B., Thromboembolic complications after treatment with monoclonal antibody against CD40 ligand. Nat Med 2000. 6: 114.

24 Daley, S. R., Cobbold, S. P. and Waldmann, H., Fc-disabled anti-mouse CD40L antibodies retain efficacy in promoting transplantation tolerance. Am J Transplant 2008. 8: 2265-2271.

25 Sanchez-Fueyo, A., Domenig, C., Strom, T. B. and Zheng, X. X., The complement dependent cytotoxicity (CDC) immune effector mechanism contributes to anti-CD154 induced immunosuppression. Transplantation 2002. 74: 898-900.

26 Monk, N. J., Hargreaves, R. E., Marsh, J. E., Farrar, C. A., Sacks, S. H., Millrain, M., Simpson, E., Dyson, J. and Jurcevic, S., Fc-dependent depletion of activated T cells occurs through CD40L-specific antibody rather than costimulation blockade. Nat Med 2003. 9: 1275-1280.

27 Truscott, S. M., Abate, G., Price, J. D., Kemper, C., Atkinson, J. P. and Hoft, D. F., CD46 engagement on human CD4+ T cells produces T regulatory type 1-like regulation of antimycobacterial T cell responses. Infection and immunity 2010. 78: 5295-5306.

28 Cardone, J., Le Friec, G., Vantourout, P., Roberts, A., Fuchs, A., Jackson, I., Suddason, T., Lord, G., Atkinson, J. P., Cope, A., Hayday, A. and Kemper, C., Complement regulator CD46 temporally regulates cytokine production by conventional and unconventional T cells. Nature immunology 2010. 11: 862-871.

29 Fuchs, A., Atkinson, J. P., Fremeaux-Bacchi, V. and Kemper, C., CD46-induced human Treg enhance B-cell responses. European journal of immunology 2009. 39: 3097-3109.

30 Alford, S. K., Longmore, G. D., Stenson, W. F. and Kemper, C., CD46-induced immunomodulatory CD4+ T cells express the adhesion molecule and chemokine receptor pattern of intestinal T cells. Journal of immunology 2008. 181: 2544-2555.

31 Barchet, W., Price, J. D., Cella, M., Colonna, M., MacMillan, S. K., Cobb, J. P., Thompson, P. A., Murphy, K. M., Atkinson, J. P. and Kemper, C., Complement-induced regulatory T cells suppress T-cell responses but allow for dendritic-cell maturation. Blood 2006. 107: 1497-1504.

32 Liszewski, M. K., Kemper, C., Price, J. D. and Atkinson, J. P., Emerging roles and new functions of CD46. Springer seminars in immunopathology 2005. 27: 345-358.

33 Kawai, T., Andrews, D., Colvin, R. B., Sachs, D. H. and Cosimi, A. B. Thromboembolic complications after treatment with monoclonal antibody against CD40 ligand [In Process Citation]. Nat Med 2000. 6: 114.

34 Langer, F., Ingersoll, S. B., Amirkhosravi, A., Meyer, T., Siddiqui, F. A., Ahmad, S., Walker, J. M., Amaya, M., Desai, H. and Francis, J. L., The role of CD40 in CD40L- and antibody-mediated platelet activation. Thrombosis and haemostasis 2005. 93: 1137-1146.

35 Robles-Carrillo, L., Meyer, T., Hatfield, M., Desai, H., Davila, M., Langer, F., Amaya, M., Garber, E., Francis, J. L., Hsu, Y. M. and Amirkhosravi, A., Anti-CD40L immune complexes potently activate platelets in vitro and cause thrombosis in FCGR2A transgenic mice. J Immunol 2010. 185: 1577-1583.

36 Couzin, J., Drug discovery. Magnificent obsession. Science 2005. 307: 1712-1715.

37 Hessell, A. J., Hangartner, L., Hunter, M., Havenith, C. E., Beurskens, F. J., Bakker, J. M., Lanigan, C. M., Landucci, G., Forthal, D. N., Parren, P. W., Marx, P. A. and Burton, D. R., Fc receptor but not complement binding is important in antibody protection against HIV. Nature 2007. 449: 101-104.

38 Armour, K. L., Clark, M. R., Hadley, A. G. and Williamson, L. M., Recombinant human IgG molecules lacking Fcgamma receptor I binding and monocyte triggering activities. Eur J Immunol 1999. 29: 2613-2624.

39 Taylor, P. A., Lees, C. J., Wilson, J. M., Ehrhardt, M. J., Campbell, M. T., Noelle, R. J. and Blazar, B. R., Combined effects of calcineurin inhibitors or sirolimus with anti-CD40L mAb on alloengraftment under nonmyeloablative conditions. Blood 2002. 100: 3400-3407.

40 Noelle, R. J., Roy, M., Shepherd, D. M., Stamenkovic, I., Ledbetter, J. A. and Aruffo, A., A novel ligand on activated T helper cells binds CD40 and transduces the signal for the cognate activation of B cells. Proc. Natl. Acad. Sci. USA 1992. 89: 6550-6554.

41 Quezada, S. A., Bennett, K., Blazar, B. R., Rudensky, A. Y., Sakaguchi, S. and Noelle, R. J., Analysis of the underlying cellular mechanisms of anti-CD154-induced graft tolerance: the interplay of clonal anergy and immune regulation. J Immunol 2005. 175: 771-779.

42 Rossini, A. A., Parker, D. C., Phillips, N. E., Durie, F. H., Noelle, R. J., Mordes, J. P. and Greiner, D. L., Induction of immunological tolerance to islet allografts. Cell Transplant 1996. 5: 49-52.

43 Markees, T., Phillips, N., Gordon, E., Noelle, R. J., Mordes, J. P., Greiner, D. L. and Rossini, A. A., Improved skin allograft tolerance induced by treatment with donor splenocytes and an extended course of anti-CD154 monoclonal antibody. Transplant Proc 1998. 30: 2444-2446.

44 Markees, T. G., Appel, M. C., Noelle, R. J., Mordes, J. P., Greiner, D. L. and Rossini, A. A., Tolerance to islet xenografts induced by dual manipulation of antigen presentation and co-stimulation. Transplantation Proceedings 1996. 28: 814-815. van den Eertwegh, A. J., Van Meurs, M., Foy, T. M., Noelle, R. J., Boersma, 45 W. J. and Claassen, E., In vivo gp39-CD40 interactions occur in the non-follicular compartments of the spleen and are essential for thymus dependent antibody responses and germinal center formation. Adv Exp Med Biol 1994. 355: 75-80.

46 van, den, Eertwegh, Aj, Van, M. M., Foy, T. M., Noelle, R. J., Boersma, W. J. and Claassen, E., In vivo gp39-CD40 interactions occur in the non-follicular compartments of the spleen and are essential for thymus dependent antibody responses and germinal center formation. Advances in experimental medicine and biology 1994. 355: 75-80.

47 Foy, T. M., Laman, J. D., Ledbetter, J. A., Aruffo, A., Claassen, E. and Noelle, R. J., gp39-CD40 interactions are essential for germinal center formation and the development of B cell memory. J. Exp. Med. 1994. 180: 157-164.

48 Gerritse, K., Laman, J. D., Noelle, R. J., Aruffo, A., Ledbetter, J. A., Boersma, W. J. and Claassen, E., CD40-

CD40 ligand interactions in experimental allergic encephalomyelitis and multiple sclerosis. National Academy of Sciences, Washington, D.c, Proceedings of the National Academy of Sciences 1996. 93: 2499-2504.

49 Nagelkerken, L., Haspels, I., van Rijs, W., Blauw, B., Ferrant, J. L., Hess, D. M., Garber, E. A., Taylor, F. R. and Burkly, L. C., FcR interactions do not play a major role in inhibition of experimental autoimmune encephalomyelitis by anti-CD154 monoclonal antibodies. J Immunol 2004. 173: 993-999.

50 Becher, B., Durell, B. G. and Noelle, R. J., Experimental autoimmune encephalitis and inflammation in the absence of interleukin-12. J Clin Invest 2002. 110: 493-497.

51 Becher, B., Durell, B. G., Miga, A. V., Hickey, W. F. and Noelle, R. J., The clinical course of experimental autoimmune encephalomyelitis and inflammation is controlled by the expression of CD40 within the central nervous system. J Exp Med 2001. 193: 967-974.

52 Howard, L. M., Miga, A. J., Vanderlugt, C. L., Dal Canto, M. C., Laman, J. D., Noelle, R. J. and Miller, S. D., Mechanisms of immunotherapeutic intervention by anti-CD40L (CD154) antibody in an animal model of multiple sclerosis. J Clin Invest 1999. 103: 281-290.

The entire disclosure of each document cited (including patents, patent applications, journal articles, abstracts, manuals, books, or other disclosures) in the Background of the Invention, Detailed Description, and Examples is herein incorporated by reference in their entireties.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

What is claimed is:

1. A nucleic acid which encodes for an antibody which binds to human CD154, which antibody comprises a variable heavy chain polypeptide comprising the amino acid sequence of SEQ ID NO: 1 and a variable light chain polypeptide comprising the amino acid sequence of SEQ ID NO: 2.

2. The nucleic acid of claim 1, wherein said nucleic acid further comprises nucleic acids encoding human IgG1, IgG2, IgG3 or IgG4 constant regions.

3. The nucleic acid of claim 1, wherein said nucleic acid further comprises nucleic acids encoding human IgG1 constant regions.

4. The nucleic acid of claim 1, wherein said nucleic acid further comprises nucleic acids encoding heavy chain and light chain constant regions of human IgG1; and wherein the heavy chain constant region comprises a E269R mutation and a K322A mutation (wherein numbering is according to Kabat).

5. The nucleic acid of claim 1, wherein said nucleic acid further comprises nucleic acids which encode heavy chain and light chain constant regions of human IgG1 respectively comprising the amino acid sequence of SEQ ID NO: 3 and the amino acid sequence of SEQ ID NO: 4.

6. A recombinant cell comprising a nucleic acid according to claim 1.

7. A method of producing an anti-human CD154 antibody comprising:

(i) introducing a nucleic acid according to claim 1 that encodes for an antibody which binds human CD154 into an isolated host cell;

(ii) culturing said host cell under conditions which provide for the expression of said antibody; and (iii) optionally isolating the resultant expressed antibody from the host cell or culture containing the host cell.

8. A method of producing an anti-human CD154 antibody according to claim 7, wherein the nucleic acid encoding the anti-human CD154 antibody further comprises nucleic acids encoding heavy chain and light chain constant regions of human IgG1; and wherein the encoded heavy chain constant region comprises a E269R mutation and a K322A mutation (wherein numbering is according to Kabat).

9. A method of producing an anti-human CD154 antibody according to claim 7, wherein the nucleic acid encoding the anti-human CD154 antibody further comprises nucleic acids encoding heavy chain and light chain constant regions of human IgG1, said heavy chain and light chain constant regions respectively comprising the amino acid sequence of SEQ ID NO: 3 and the amino acid sequence of SEQ ID NO: 4.

* * * * *